United States Patent
Goshima et al.

(10) Patent No.: US 11,124,474 B2
(45) Date of Patent: Sep. 21, 2021

(54) DIAMINE COMPOUND, AND POLYIMIDE COMPOUND AND MOLDED PRODUCT USING THE SAME

(71) Applicant: WINGO TECHNOLOGY CO., LTD., Okayama (JP)

(72) Inventors: Toshiyuki Goshima, Okayama (JP); Win Maw Soe, Okayama (JP)

(73) Assignee: WINGO TECHNOLOGY CO., LTD., Okayama (JP)

( * ) Notice: Subject to any disclaimer, the term of this patent is extended or adjusted under 35 U.S.C. 154(b) by 0 days.

(21) Appl. No.: 16/868,705

(22) Filed: May 7, 2020

(65) Prior Publication Data

US 2020/0262783 A1 Aug. 20, 2020

Related U.S. Application Data

(62) Division of application No. 16/481,090, filed as application No. PCT/JP2018/001205 on Jan. 17, 2018, now Pat. No. 10,683,259.

(30) Foreign Application Priority Data

| Jan. 27, 2017 | (JP) | 2017-013567 |
| Jan. 27, 2017 | (JP) | 2017-013580 |
| Nov. 24, 2017 | (JP) | 2017-226242 |
| Nov. 24, 2017 | (JP) | 2017-226250 |

(51) Int. Cl.

| C08G 73/10 | (2006.01) |
| C07C 229/60 | (2006.01) |
| C07C 201/12 | (2006.01) |
| C07C 227/04 | (2006.01) |
| C08G 69/26 | (2006.01) |
| C08G 73/16 | (2006.01) |

(52) U.S. Cl.
CPC .......... *C07C 229/60* (2013.01); *C07C 201/12* (2013.01); *C07C 227/04* (2013.01); *C08G 69/26* (2013.01); *C08G 73/105* (2013.01); *C08G 73/1067* (2013.01); *C08G 73/1071* (2013.01); *C08G 73/16* (2013.01)

(58) Field of Classification Search
CPC ... C09D 179/08; C08L 79/08; C08G 73/1071; C08G 73/10; C08J 2379/08
See application file for complete search history.

(56) References Cited

U.S. PATENT DOCUMENTS

2011/0165809 A1    7/2011    Miyauchi et al.

FOREIGN PATENT DOCUMENTS

| JP | H3-103441 A | 4/1991 |
| JP | H5-214101 A | 8/1993 |
| JP | H7-133349 A | 5/1995 |
| JP | 2003-238684 A | 8/2003 |
| JP | 2007-112990 A | 5/2007 |
| JP | 2007-169585 A | 7/2007 |
| JP | 2008-255252 A | 10/2008 |
| JP | WO 2010110335 | * 9/2010 |
| JP | 2014-173071 A | 9/2014 |
| JP | 6240798 B1 | 11/2017 |
| JP | 6240799 B1 | 11/2017 |
| WO | 2010027020 A1 | 3/2010 |
| WO | 2010093021 A1 | 8/2010 |
| WO | 2013144991 A1 | 10/2013 |

OTHER PUBLICATIONS

USPTO structure search, May 2021.*
Suh Synthesis and Characterization of Chemically Modified Aromatic Poly(ester-amide)s Exhibiting Liquid Crystalline Properties in Organic Solvent, Seoul National University, published on Aug. 2015.*
Hasegawa et al Poly(ester imide)s possessing low coefficients of thermal expansion (GTE) and low water absorption (III). Use of bis (4-aminophenyl)terephthalate and effect of substituents, European Polymer Journal 46 (2010) 1510-1524, published Apr. 18, 2010.*
Nov. 13, 2020—(JP) Office Action—App No. 2017-226250.
Oct. 16, 2020—(EP) European Search Report—App No. 18744339.5.
Masatoshi Hasegawa et al. "gamma-Butyrolactone-processable high-modulus poly(estr imide)s" Polymer International, vol. 61, No. 3, Nov. 10, 2011, pp. 466-476, XP05370803, Josh Wiley & Sons, New York, NY, US ISSN: 0959-8103, DOI: 10.1002/pi.3199.

(Continued)

*Primary Examiner* — Gregory Listvoyb
(74) *Attorney, Agent, or Firm* — Banner & Witcoff, Ltd.

(57) ABSTRACT

[Problems to be Solved] The present invention provides a novel diamine compound which allows for the synthesis of a polyimide compound having a high solubility in an organic solvent and a high melt moldability.

[Solution] The diamine compound according to the present invention is characterized by being represented by the following general formula (1):

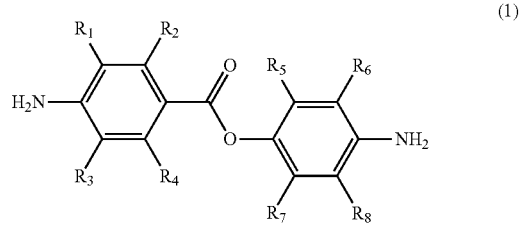

(1)

(wherein
R$_1$ to R$_8$ are each independently selected from the group consisting of a hydrogen atom, a fluorine atom, a substituted or unsubstituted alkyl group, and a substituted or unsubstituted aromatic group; and at least one of R$_1$ to R$_8$ is a substituted or unsubstituted aromatic group).

7 Claims, 3 Drawing Sheets

(56) References Cited

OTHER PUBLICATIONS

Masatoshi Hasegawa et al. "Poly(ester imide)s possessing low coefficients of thermal expansion (CTE) and low water absorption (III). Use of bis(4-aminophenyl) terephthalate and effect of substituents" European Polymer Journal, vol. 46, No. 7, Apr. 18, 2010, pp. 1510-1524, XP027096600, Elsevier, Oxford, GB ISSN: 0014-3057, DOI: 10.1016/j.eurpolymj.2010.04.014.
May 30, 2017 (JP) Office Action App. No. 2017-013567.
Aug. 25, 2017 (JP) Office Action App. No. 2017-013567.
May 30, 2017 (JP) Office Action App. No. 2017-013580.
Aug. 25, 2017 (JP) Office Action App. No. 2017-013580.
Morikawa et al. "Synthesis and Characterization of Novel Aromatic Polyimides from Bis(4-amino-2-biphenyl)ether and Aromatic Tetracarboxylic Dianhydrides" Polymer Journal, vol. 37, No. 10, pp. 759-766 (2005.).
Nov. 20, 2019 (CN) Office Action Applicantion No. 201880001194.3.
Volozhin et al. Relative reactivity of aromatic diamines in polyamic acid formation. Doklady Akademii Nauk BSSR, vol. 32, No. 8, pp. 726-728, Aug. 16, 2006.

\* cited by examiner 3405 cm⁻¹, 3332 cm⁻¹ Amine N-H stretching
3056 cm⁻¹, 3037 cm⁻¹ Aromatic C-H stretching
1706 cm⁻¹: Ester C=O stretching
1595 cm⁻¹: Amine N-H bending
1620 cm⁻¹, 1512 cm⁻¹: Aromatic C=C stretching
1310 cm⁻¹: Amine C-N stretching
1273 cm⁻¹: Ester antisymmetric C-O-C stretching

DIAMINE COMPOUND, AND POLYIMIDE COMPOUND AND MOLDED PRODUCT USING THE SAME

RELATED APPLICATION DATA

This application is a divisional application which claims priority to U.S. patent application Ser. No. 16/481,090, filed on Jul. 26, 2019, which is a National Stage Application under 35 U.S.C. 371 of co-pending PCT application number PCT/JP2018/001205 designating the United States and filed January 17, 2018; which claims the benefit of JP application no. 2017-013580, filed Jan. 27, 2017, JP application no. 2017-013567, filed Jan. 27, 2017, JP application no. 2017-226250, filed Nov. 24, 2017, and JP application no. 2017-226242, filed Nov. 24, 2017 each of which are hereby incorporated by reference in their entireties.

BACKGROUND OF THE INVENTION

Field of the Invention

The present invention relates to a novel diamine compound. More particularly, the present invention relates to a novel diamine compound which allows for the synthesis of a polyimide compound having an improved solubility in an organic solvent and an improved melt moldability; as well as to a polyimide compound synthesized using the same; and a molded product including the polyimide compound.

Background Art

In general, polyimide compounds have an excellent mechanical strength, wear resistance, dimensional stability, chemical resistance, electrical insulation properties and the like, in addition to having a high heat resistance, and thus are widely used in the field of electronic materials, such as flexible printed circuit boards and printed wiring boards. In addition to the field of electronic devices, polyimide compounds are also widely used in the fields of space and aviation, automobiles and the like. Among these polyimide compounds, polyimide compounds formed from an aromatic diamine and an aromatic acid anhydride, as raw materials, are known to have an excellent mechanical strength and heat resistance. For example, a polyimide compound formed from an aromatic diamine, such as 4-aminophenyl-4-aminobenzoate, and pyromellitic dianhydride, as raw materials, has an excellent heat resistance, mechanical properties, electrical insulation and the like, and is suitably used as a protective material or an insulating material in the field of electronic devices (see, for example, Patent Document 1).

However, the above described aromatic polyimide compound has a low solubility in an organic solvent, due to having a rigid structure. Therefore, in the case of producing a cover film for a flexible printed wiring substrate (FPC), an insulating layer for an electronic circuit or the like, the production thereof has been carried out, not by using the polyimide compound, but by the following method. Specifically, the production has been carried out by allowing a diamine compound to react with an acid anhydride in an organic solvent, to obtain a polyamic acid solvent which contains a polyamic acid having a high solubility in an organic solvent, and coating the resulting solvent on a substrate or the like, followed by heat drying at a high temperature to allow a cyclodehydration reaction (polyimidization) to occur (see, for example, Patent Document 1).

PRIOR ART DOCUMENT

Patent Document

Patent Document 1: JP 2014-173071 A

SUMMARY OF THE INVENTION

Problems to be Solved by the Invention

However, the substrate on which a polyimide film is to be formed needs to have a high heat resistance capable of withstanding the cyclodehydration reaction (withstanding a temperature of from 300 to 400° C., in general). Further, such a production must be carried out under an environment where a special heating apparatus for carrying out the cyclodehydration reaction can be used. Thus, there are various limitations in the production of a molded article using a polyimide compound. In addition, polyamic acid compounds have problems that they are unstable, react with water, are easily hydrolyzed, and are susceptible to a decrease in molecular weight.

Moreover, most of polyimide compounds do not have a melting point, and even those having a melting point have a very low melting point, making it difficult to carry out melt molding. Therefore, there is also a problem in melt moldability.

The present invention has been made in view of the above described problems. An object of the present invention is to provide: a novel diamine compound which allows for the synthesis of a polyimide compound having a high solubility in an organic solvent and a high melt moldability; and a method of synthesizing the diamine compound.

Another object of the present invention is to provide a polyimide compound having a high solubility in an organic solvent and a high melt moldability, which is synthesized using the above described diamine compound.

Still another object of the present invention is to provide a molded product, such as, for example, a polyimide film, which includes the above described polyimide compound, and which has a heat resistance and mechanical properties comparable to a polyimide film including a conventional polyimide compound.

Means for Solving the Problems

The diamine compound according to the present invention is characterized by being represented by the following general formula (1):

[Chem. 1]

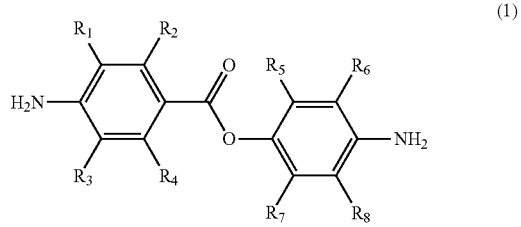

(wherein
$R_1$ to $R_8$ are each independently selected from the group consisting of a hydrogen atom, a fluorine atom, a substituted or unsubstituted alkyl group, and a substituted or unsubstituted aromatic group; and at least one of $R_1$ to $R_8$ is a substituted or unsubstituted aromatic group).

In the above described embodiment, at least one or two of $R_5$ to $R_8$ is/are (each) preferably a substituted or unsubstituted aromatic group.

In the above described embodiment, one or two of $R_5$ to $R_8$ is/are (each) preferably a substituted or unsubstituted aromatic group, and $R_1$ to $R_8$ other than the aromatic group(s) are each preferably selected from the group consisting of a hydrogen atom, a fluorine atom, and a substituted or unsubstituted alkyl group.

In the above described embodiment, the substituted or unsubstituted aromatic group preferably has from 5 to 20 carbon atoms.

In the above described embodiment, the substituted or unsubstituted aromatic group is preferably selected from the group consisting of a phenyl group, a methylphenyl group, a phenoxy group, a benzyl group and a benzyloxy group.

The method of synthesizing the diamine compound according to the present invention includes the steps of:

allowing a compound represented by the following general formula (3):

[Chem. 2]

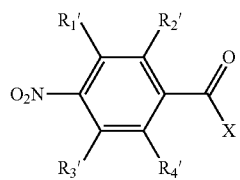

(3)

to react with a compound represented by the following general formula (4):

[Chem. 3]

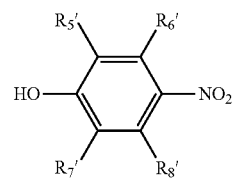

(4)

to obtain a reaction product; and
reducing the nitro group in the reaction product
(wherein
$R_1$ to $R_8$ are each independently selected from the group consisting of a hydrogen atom, a fluorine atom, a substituted or unsubstituted alkyl group, and a substituted or unsubstituted aromatic group;
at least one of $R_1$ to $R_8$ is a substituted or unsubstituted aromatic group;
$R_1'$ to $R_8'$ are each independently selected from the group consisting of a hydrogen atom, a fluorine atom, a substituted or unsubstituted alkyl group, and a substituted or unsubstituted aromatic group; and
at least one of $R_1'$ to $R_8'$ is an aromatic group).

The polyimide compound according to the present invention is characterized by being a reaction product of the above described diamine compound with an acid anhydride.

In the above described embodiment, the acid anhydride is preferably represented by the following general formula(e) (8) and/or (9):

[Chem. 4]

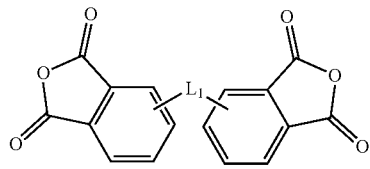

(8)

[Chem. 5]

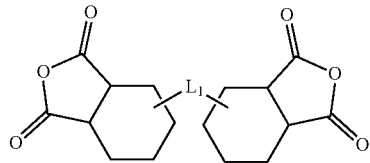

(9)

(wherein
$L_1$ represents a linking group selected from the following group of linking groups:

[Chem. 6]

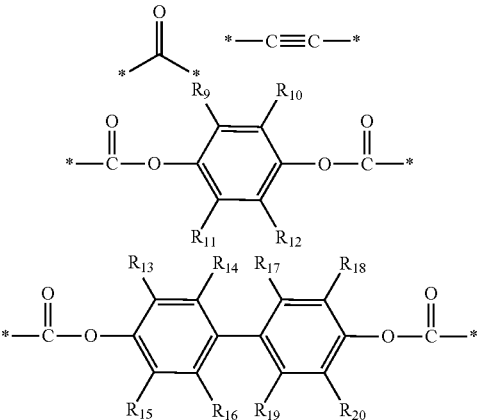

wherein
$R_9$ to $R_{20}$ are each independently selected from the group consisting of a hydrogen atom, a substituted alkyl group and an unsubstituted alkyl group; and * represents a binding position).

In the above described embodiment, the acid anhydride is preferably represented by the following general formula(e) (8) and/or (9):

[Chem. 7]

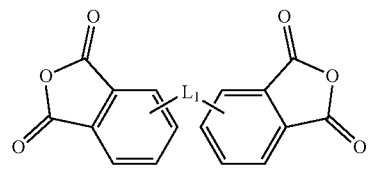

(8)

-continued

[Chem. 8]

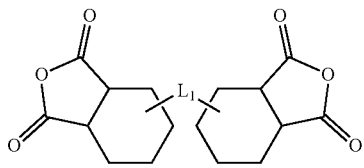

(9)

wherein
L₁ represents a linking group selected from the following group of linking groups:

[Chem. 9]

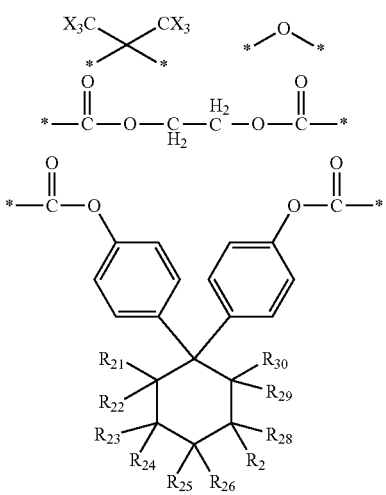

wherein
X represents a halogen group selected from a fluoro group, a chloro group, a bromo group and an iodo group;
$R_{21}$ to $R_{30}$ are each independently selected from the group consisting of a hydrogen atom, a substituted alkyl group and an unsubstituted alkyl group; and
* represents a binding position).

The molded product according to the present invention is characterized by including the above described polyimide compound.

Effect of the Invention

The diamine compound according to the present invention enables to markedly improve the solubility in an organic solvent and the melt moldability of a polyimide compound synthesized using the diamine compound, and to produce a molded article of the polyimide compound without taking into consideration the heat resistance or the like of the substrate to be used therefor.

Further, it becomes possible to produce the molded article in various places, since there is no need to use a special apparatus for carrying out a heat treatment, in the production of the molded article.

Still further, the molded product according to the present invention has a 5% by weight reduction ratio, a glass transition temperature (Tg), a melting temperature, a thermal expansion coefficient, a tensile strength, an elastic modulus and a water absorption rate, which are comparable to those of a molded product produced using a conventional polyimide compound, as well as a high heat resistance and high mechanical properties. Therefore, the molded product according to the present invention can be used in various fields, such as the fields of: electronic devices, space and aviation, automobiles, etc.

Figure 1:
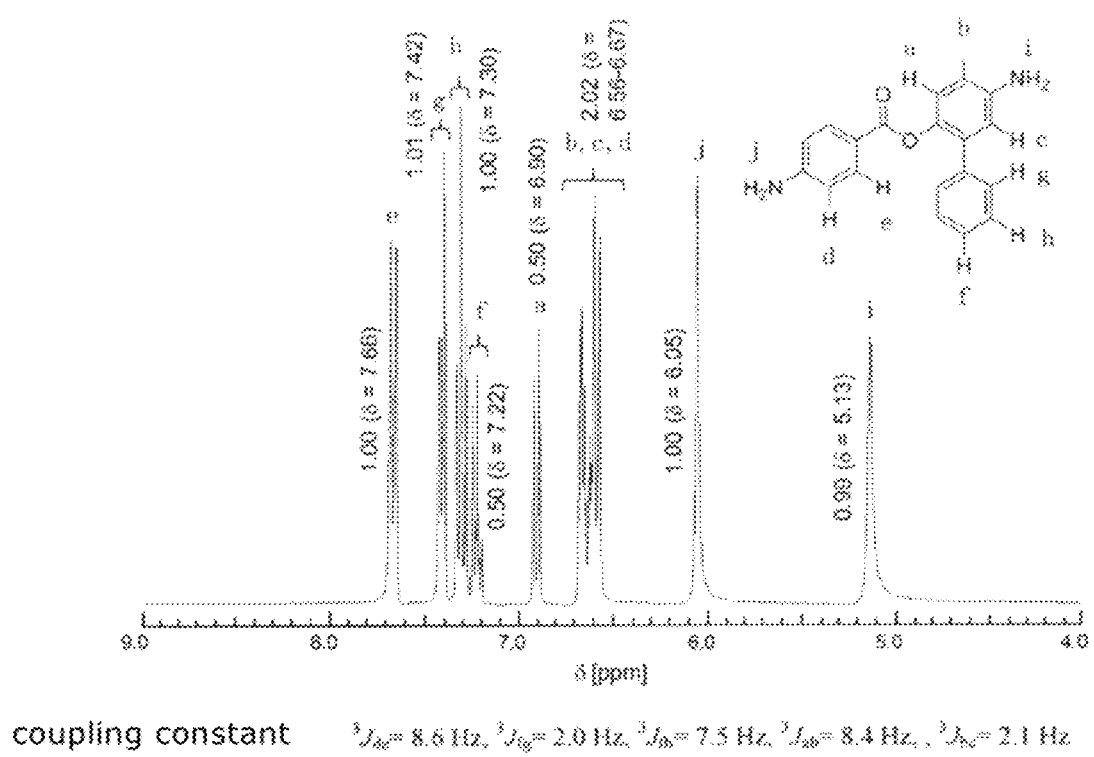
FIG. 1 is a ¹H-NMR chart of a compound obtained in Examples and represented by chemical formula (2).

DETAILED DESCRIPTION OF THE INVENTION (Diamine Compound)
The diamine compound according to the present invention is characterized by being represented by the following general formula (1):

[Chem. 10]

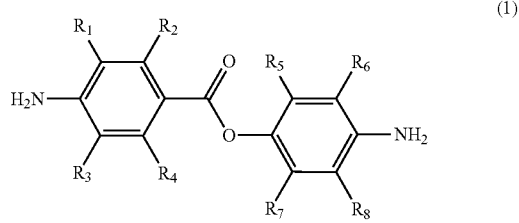

(1)

In the above described formula, $R_1$ to $R_8$ are each independently selected from the group consisting of a hydrogen atom, a fluorine atom, a substituted or unsubstituted alkyl group, and a substituted or unsubstituted aromatic group; and at least one of $R_1$ to $R_8$ is an aromatic group. Preferably, one or two of $R_1$ to $R_8$ is/are (each) an aromatic group.

Preferably, one or two of $R_5$ to $R_8$ is/are (each) a substituted or unsubstituted aromatic group, and more preferably, at least $R_5$ or $R_7$ is an aromatic group.

When the diamine compound has an aromatic group(s) at the above described position(s), the steric hindrance of the diamine compound can be reduced, as a result of which a polymerization reaction with an acid anhydride or the like can be carried out in a favorable manner.

In a particularly preferred embodiment, one or two of $R_5$ to $R_8$ is/are (each) a substituted or unsubstituted aromatic group, and $R_1$ to $R_8$ other than the aromatic group(s) are each selected from the group consisting of a hydrogen atom, a fluorine atom, and a substituted or unsubstituted alkyl group. Specific examples include a compound represented by the following formula (2) (an embodiment in which $R_7$ is an aromatic group; and $R_1$ to $R_6$ and $R_8$ other than $R_7$ are each a hydrogen atom).

[Chem. 11]

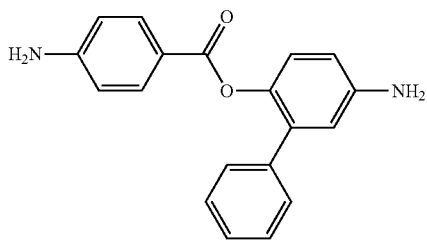

(2)

In the present invention, the definition of the alkyl group includes a linear alkyl group, a branched alkyl group and a cyclic alkyl group. Further, an alkoxy group and an alkylamino group, each of which binds to the main skeleton via an oxygen atom or a nitrogen atom, is also included in the definition.

Likewise, the definition of the aromatic group includes a substituent which binds to the main skeleton via an oxygen atom, a nitrogen atom, or a carbon atom. Further, the definition of the aromatic group further includes a heteroaromatic group, such as pyrrole group.

The alkyl group and the aromatic group are preferably unsubstituted, from the viewpoint of facilitating the synthesis of the diamine compound according to the present invention, and the application of the compound in the field of electronic component materials. However, the alkyl group and the aromatic group may have a substituent, and examples of the substituent include: alkyl groups; halogen groups such as fluoro group and chloro group; amino group; nitro group; hydroxyl group; cyano group; carboxyl group; and sulfonic acid group. The alkyl group and the aromatic group may be a group having one or more, or two or more of these substituents.

The alkyl group preferably has from 1 to 10 carbon atoms, and more preferably from 1 to 3 carbon atoms.

Examples of the alkyl group having from 1 to 10 carbon atoms include: methyl group, ethyl group, n-propyl group, isopropyl group, n-butyl group, tert-butyl group, n-pentyl group, sec-pentyl group, n-hexyl group, cyclohexyl group, n-heptyl group, n-octyl group, n-nonyl group, n-decyl group, fluoromethyl group, difluoromethyl group, trifluoromethyl group, chloromethyl group, dichloromethyl group, trichloromethyl group, bromomethyl group, dibromomethyl group, tribromomethyl group, fluoroethyl group, difluoroethyl group, trifluoroethyl group, chloroethyl group, dichloroethyl group, trichloroethyl group, bromoethyl group, dibromoethyl group, tribromoethyl group, hydroxymethyl group, hydroxyethyl group, hydroxylpropyl group, methoxy group, ethoxy group, n-propoxy group, n-butoxy group, n-pentyloxy group, sec-pentyloxy group, n-hexyloxy group, cyclohexyloxy group, n-heptyloxy group, n-octyloxy group, n-nonyloxy group, n-decyloxy group, trifluoromethoxy group, methylamino group, dimethylamino group, trimethylamino group, ethylamino group, and propylamino group.

Among the above described alkyl groups, methyl group, ethyl group, methoxy group, ethoxy group and trifluoromethyl group are preferred, from the viewpoint of steric hindrance and heat resistance.

The aromatic group preferably has from 5 to 20 carbon atoms, and more preferably from 6 to 10 carbon atoms.

Examples of the aromatic group having from 5 to 20 carbon atoms include: phenyl group, tolyl group, methylphenyl group, dimethylphenyl group, ethylphenyl group, diethylphenyl group, propylphenyl group, butylphenyl group, fluorophenyl group, pentafluorophenyl group, chlorphenyl group, bromophenyl group, methoxyphenyl group, dimethoxyphenyl group, ethoxyphenyl group, diethoxyphenyl group, benzyl group, methoxybenzyl group, dimethoxybenzyl group, ethoxybenzyl group, diethoxybenzyl group, aminophenyl group, aminobenzyl group, nitrophenyl group, nitrobenzyl group, cyanophenyl group, cyanobenzyl group, phenethyl group, phenylpropyl group, phenoxy group, benzyloxy group, phenylamino group, diphenylamino group, biphenyl group, naphthyl group, phenylnaphthyl group, diphenylnaphthyl group, anthryl group, anthrylphenyl group, phenylanthryl group, naphthacenyl group, phenanthryl group, phenanthrylphenyl group, phenylphenanthryl group, pyrenyl group, phenylpyrenyl group, fluorenyl group, phenylfluorenyl group, naphthylethyl group, naphthylpropyl group, anthracenylethyl group, and phenanthrylethyl group; and heteroaromatic groups such as pyrrole group, imidazole group, thiazole group, oxazole group, furan group, thiophene group, triazole group, pyrazole group, isoxazole group, isothiazole group, pyridine group, pyrimidine group, benzofuran group, benzothiophene group, quinolone group, isoquinolone group, indolyl group, benzothiazolyl group, and carbazolyl group.

Among the above described aromatic groups, phenyl group, phenoxy group, benzyl group and benzyloxy group are preferred, from the viewpoint of the availability of starting raw materials and the cost of synthesis.

(Method of Synthesizing Diamine Compound)

The diamine compound according to the present invention can be obtained by allowing a compound represented by the following general formula (3):

[Chem. 12]

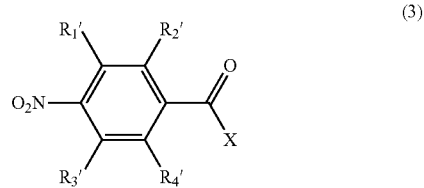

(3)

to react with a compound represented by the following general formula (4):

[Chem. 13]

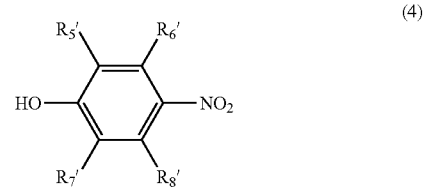

(4)

and then reducing the nitro group.

In the above described formulae, $R_1'$ to $R_8'$ are each independently selected from the group consisting of a hydrogen atom, a substituted or unsubstituted alkyl group, and a substituted or unsubstituted aromatic group; and at least one of $R_1'$ to $R_8'$ is an aromatic group.

Preferably, at least one of $R_5'$ to $R_8'$ is a substituted or unsubstituted aromatic group, and more preferably, at least $R_5'$ or $R_7'$ is an aromatic group.

In a particularly preferred embodiment, one of $R_5'$ to $R_8'$ is a substituted or unsubstituted aromatic group, and $R_1'$ to $R_8'$ other than the aromatic group are each a hydrogen atom.

Further, in the above described formula (3), X represents a hydroxyl group, or a halogen group selected from a fluoro group, a chloro group, a bromo group and an iodo group. From the viewpoint of the reactivity with the compound represented by the general formula (4), X is preferably a halogen group, and particularly preferably a chloro group or a bromo group.

In cases where X in the general formula (3) is a hydroxyl group, the reaction of the compound represented by the general formula (3) with the compound represented by general formula (4) is preferably carried out in the presence of a catalyst or a dehydration condensation agent.

Examples of the catalyst include: organic and inorganic basic compounds such as dimethylamino pyridine, tri-n-butylamine, pyridine, lysine, imidazole, sodium carbonate, sodium alcoholate and potassium hydrogen carbonate; organic acids such as toluenesulfonic acid, methanesulfonic acid and sulfuric acid; and inorganic acids.

Examples of the dehydration condensation agent include: carbodiimides such as N,N'-dicyclohexylcarbodiimide (DCC), N,N'-diisopropylcarbodiimide and N-cyclohexyl-N'-(4-diethylamino)cyclohexylcarbodiimide.

Further, in cases where X in the general formula (3) is a halogen group, the reaction of the compound represented by the general formula (3) with the compound represented by general formula (4) is preferably carried out in the presence of an acid acceptor. Specific examples of the acid acceptor include: trialkylamines such as triethylamine, tributylamine and N,N-dimethylcyclohexylamine; aliphatic cyclic tertiary amines such as N-methylmorpholine; aromatic amines such as N,N-dimethylaniline and triphenylamine; and heterocyclic amines such as pyridine, picoline, lutidine and quinolone.

More specifically, the diamine compound represented by the above described formula (2) can be obtained by allowing a compound represented by the following formula (5):

[Chem. 14]

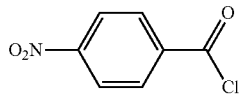
(5)

to react with a compound represented by the formula (6):

[Chem. 15]

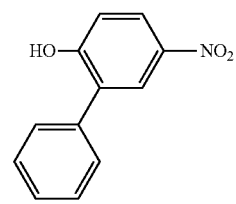
(6)

The compound represented by the general formula (4) can be obtained by nitration of a compound represented by the following general formula (7) which is commercially available or synthesized. The nitration of the compound represented by the following general formula (7) can be carried out by a conventionally known nitration method, using a mixed acid of concentrated sulfuric acid and concentrated nitric acid, nitric acid, fuming nitric acid, an acid alkali metal salt in concentrated sulfuric acid, acetyl nitrate, a nitronium salt, a nitrogen oxide and the like.

[Chem. 16]

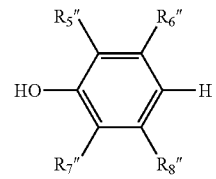
(7)

$R_5''$ to $R_8''$ are each independently selected from the group consisting of a hydrogen atom, a substituted or unsubstituted alkyl group, and a substituted or unsubstituted aromatic group. Preferably, at least one of $R_5''$ to $R_8''$ is an aromatic group, and more preferably one or two of $R_5''$ to $R_8''$ is/are (each) an aromatic group.

The diamine compound according to the present invention can also be used in the synthesis of a compound other than the polyimide compound to be described later.

For example, it is possible to synthesize a polyamide compound by reacting the diamine compound with: terephthalic acid, isophthalic acid, naphthalenedicarboxylic acid, diphenyl ether carboxylic acid, diphenylsulfonecarboxylic acid, biphenyldicarboxylic acid, terphenyldicarboxylic acid, diphenylmethanedicarboxylic acid, 2,2-bis(4-carboxyphenyl)propane, 2,2-bis(4-carboxyphenyl)hexafluoropropane, cyclohexanedicarboxylic acid or dicyclohexanedicarboxylic acid, or with a dicarboxylic acid derivative such as an acid halide thereof.

Further, the diamine compound according to the present invention can also be used in the synthesis of a polyamide-imide compound, a polyurethane compound, or an epoxy compound.

(Polyimide Compound)

The polyimide compound according to the present invention is a reaction product of the diamine compound represented by the above described general formula (1) with an acid anhydride. The structure of the diamine compound represented by the general formula (1) has already been described above, and is thus omitted here.

When the diamine compound represented by the above described general formula (1) is used as a component of the polyimide compound, it is possible to markedly improve the solubility of the polyimide compound in an organic solvent.

In the polyimide compound according to the present invention, the content of the diamine compound represented by the above described general formula (1) in the total diamine components is preferably from 10% by mole to 100% by mole, more preferably from 30% by mole to 100% by mole, and still more preferably from 50% by mole to 100% by mole. When the content of the diamine compound is adjusted within the above described numerical range, it is possible to introduce a rigid ester structure into the resulting polyimide compound, and to further improve the solubility of the polyimide compound in an organic solvent.

The polyimide compound according to the present invention preferably has a number average molecular weight of from 2,000 to 200,000, and more preferably from 4,000 to 100,000.

In the present invention, the number average molecular weight refers to a molecular weight in terms of polystyrene, which is obtained based on a calibration curve prepared by a gel permeation chromatography (GPC) apparatus, using standard polystyrene.

When the number average molecular weight is adjusted within the above described numerical range, it is possible to improve the mechanical properties of a film obtained using the resulting polyimide compound, as well as to improve the moldability of the polyimide compound.

The polyimide compound according to the present invention preferably has a melting point of 150° C. or higher and 420° C. or lower, more preferably 200° C. or higher and 350° C. or lower, from the viewpoint of improving the heat resistance of the resulting molded product, as well as the productivity and the cost of the molded product.

(Acid Anhydride)

Examples of the acid anhydride include oxydiphthalic dianhydride, pyromellitic dianhydride, 3-fluoropyromellitic dianhydride, 3,6-difluoropyromellitic dianhydride, 3,6-bis(trifluoromethyl)pyromellitic dianhydride, 1,2,3,4-benzenetetracarboxylic dianhydride, 2,2',3,3'-benzophenonetetracarboxylic dianhydride, 3,3',4,4'-benzophenonetetracarboxylic dianhydride, 3,3',4,4'-biphenyltetracarboxylic dianhydride, 3,3',4,4'-biphenylsulfonetetracarboxylic dianhydride, 4,4'-(4,4'-isopropylidenediphenoxy)bisphthalic dianhydride, 1,2,4,5-cyclohexanetetracarboxylic dianhydride, 2,3,3',4'-biphenyltetracarboxylic dianhydride, 3,3'',4,4''-terphenyltetracarboxylic dianhydride, 3,3''',4,4'''-quaterphenyltetracarboxylic dianhydride, 2,2',3,3'-biphenyltetracarboxylic dianhydride, methylene-4,4'-diphthalic dianhydride, 1,1-ethynylidene-4,4'-diphthalic dianhydride, 2,2-propylidene-4,4'-diphthalic dianhydride, 1,2-ethylene-4,4'-diphthalic dianhydride, 1,3-trimethylene-4,4'-diphthalic dianhydride, 1,4-tetramethylene-4,4'-diphthalic dianhydride, 1,5-pentamethylene-4,4'-diphthalic dianhydride, 1,3-bis[2-(3,4-dicarboxyphenyl)-2-propyl]benzene dianhydride, 1,4-bis[2-(3,4-dicarboxyphenyl)-2-propyl]benzene dianhydride, bis[3-(3,4-dicarboxyphenoxy)phenyl]methane dianhydride, bis[4-(3,4-dicarboxyphenoxy)phenyl]methane dianhydride, 2,2-bis[3-(3,4-dicarboxyphenoxy)phenyl]propane dianhydride, 2,2-bis[4-(3,4-dicarboxyphenoxy)phenyl]propane dianhydride, difluoromethylene-4,4'-diphthalic dianhydride, 1,1,2,2-tetrafluoro-1,2-ethylene-4,4'-diphthalic dianhydride, 3,3',4,4'-diphenylsulfonetetracarboxylic dianhydride, oxy-4,4'-diphthalic dianhydride, bis(3,4-dicarboxyphenyl) ether dianhydride, thio-4,4'-diphthalic dianhydride, sulfonyl-4,4'-diphthalic dianhydride, 1,3-bis(3,4-dicarboxyphenyl)benzene dianhydride, 1,4-bis(3,4-dicarboxyphenyl)benzene dianhydride, 1,3-bis(3,4-dicarboxyphenoxy)benzene dianhydride, 1,4-bis(3,4-dicarboxyphenoxy)benzene dianhydride, bis(3,4-dicarboxyphenoxy)dimethylsilane dianhydride, 1,3-bis(3,4-dicarboxyphenoxy)-1,1,3,3-tetramethyldisiloxane dianhydride, 2,3,6,7-naphthalenetetracarboxylic dianhydride, 1,2,5,6-naphthalenetetracarboxylic dianhydride, 3,4,9,10-perylenetetracarboxylic dianhydride, 2,3,6,7-anthracenetetracarboxylic dianhydride, 1,2,7,8-phenanthrenetetracarboxylic dianhydride, 1,2,3,4-butanetetracarboxylic dianhydride, 1,2,3,4-cyclobutanetetracarboxylic dianhydride, cyclopentanetetracarboxylic dianhydride, cyclohexane-1,2,3,4-tetracarboxylic dianhydride, cyclohexane-1,2,4,5-tetracarboxylic dianhydride, 3,3',4,4'-bicyclohexyltetracarboxylic dianhydride, carbonyl-4,4'-bis(cyclohexane-1,2-dicarboxylic acid) dianhydride, methylene-4,4'-bis(cyclohexane-1,2-dicarboxylic acid) dianhydride, 1,2-ethylene-4,4'-bis(cyclohexane-1,2-dicarboxylic acid) dianhydride, oxy-4,4'-bis(cyclohexane-1,2-dicarboxylic acid) dianhydride, thio-4,4'-bis(cyclohexane-1,2-dicarboxylic acid) dianhydride, sulfonyl-4,4'-bis(cyclohexane-1,2-dicarboxylic acid) dianhydride, 3,3',5,5'-tetrakis(trifluoromethyl)oxy-4,4'-diphthalic dianhydride, 3,3',6,6'-tetrakis(trifluoromethyl)oxy-4,4'-diphthalic dianhydride, 5,5',6,6'-tetrakis(trifluoromethyl)oxy-4,4'-diphthalic dianhydride, 3,3',5,5',6,6'-hexakis(trifluoromethyl)oxy-4,4'-diphthalic dianhydride, 3,3'-difluorosulfonyl-4,4'-diphthalic dianhydride, 5,5'-difluorosulfonyl-4,4'-diphthalic dianhydride, 6,6'-difluorosulfonyl-4,4'-diphthalic dianhydride, 3,3',5,5',6,6'-hexafluorosulfonyl-4,4'-diphthalic dianhydride, 3,3'-bis(trifluoromethyl)sulfonyl-4,4'-diphthalic dianhydride, 5,5'-bis(trifluoromethyl)sulfonyl-4,4'-diphthalic dianhydride, 6,6'-bis(trifluoromethyl)sulfonyl-4,4'-diphthalic dianhydride, 3,3',5,5'-tetrakis(trifluoromethyl)sulfonyl-4,4'-diphthalic dianhydride, 3,3',6,6'-tetrakis(trifluoromethyl)sulfonyl-4,4'-diphthalic dianhydride, 5,5',6,6'-tetrakis(trifluoromethyl)sulfonyl-4,4'-diphthalic dianhydride, 3,3',5,5',6,6'-hexakis(trifluoromethyl)sulfonyl-4,4'-diphthalic dianhydride, 3,3'-difluoro-2,2-perfluoropropylidene-4,4'-diphthalic dianhydride, 5,5'-difluoro-2,2-perfluoropropylidene-4,4'-diphthalic dianhydride, 6,6'-difluoro-2,2-perfluoropropylidene-4,4'-diphthalic dianhydride, 3,3',5,5',6,6'-hexafluoro-2,2-perfluoropropylidene-4,4'-diphthalic dianhydride, 3,3'-bis(trifluoromethyl)-2,2-perfluoropropylidene-4,4'-diphthalic dianhydride, and ethylene glycol bistrimellitate dianhydride.

Among the above described anhydrides, pyromellitic dianhydride, 3,3',4,4'-biphenyltetracarboxylic dianhydride, 2,2-bis[3-(3,4-dicarboxyphenoxy)phenyl]propane dianhydride, 2,2-bis[4-(3,4-dicarboxyphenoxy)phenyl]propane dianhydride and 3,3',4,4'-diphenylsulfonetetracarboxylic dianhydride, oxy-4,4'-diphthalic dianhydride are preferred, from the viewpoint of improving the reactivity with the diamine compound according to the present invention.

One kind, or two or more kinds of the above described anhydrides may be used in the synthesis of the polyimide compound according to the present invention.

In one embodiment, the polyimide compound according to the present invention is a reaction product of the diamine compound represented by the above described general formula (1) with an acid anhydride(s) represented by the following general formula(e) (8) and/or (9):

[Chem. 17]

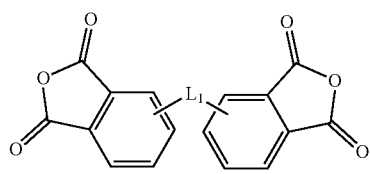

(8)

[Chem. 18]

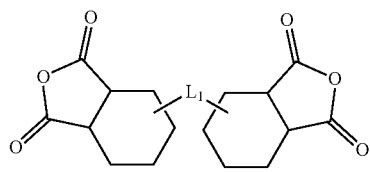

(9)

In one embodiment, $L_1$ in the above described formulae represents a linking group selected from the following group of linking groups. The polyimide compound, which is a reaction product of an acid anhydride having a linking group selected from the following group of linking groups, with the diamine compound represented by the general formula (1), has a low melting temperature, and has an extremely excellent melt moldability.

[Chem. 19]

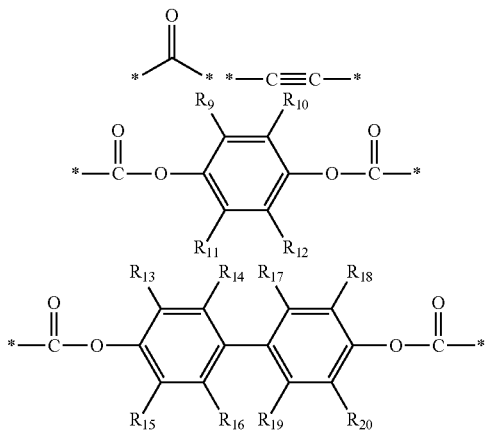

In the above described formulae, $R_9$ to $R_{20}$ are each independently selected from the group consisting of a hydrogen atom, a substituted alkyl group and an unsubstituted alkyl group; and * represents a binding position.

The alkyl group is preferably unsubstituted, from the viewpoint of facilitating the synthesis of the diamine compound according to the present invention, and the application of the compound in the field of electronic component materials. However, the alkyl group may have a substituent, and examples of the substituent include: alkyl groups; halogen groups such as fluoro group and chloro group; amino group; nitro group; hydroxyl group; cyano group; carboxyl group; and sulfonic acid group. The alkyl group and the aromatic group may be a group having one or more, or two or more of these substituents.

The alkyl group preferably has from 1 to 10 carbon atoms, and more preferably from 1 to 3 carbon atoms.

Examples of the alkyl group having from 1 to 10 carbon atoms include: methyl group, ethyl group, n-propyl group, isopropyl group, n-butyl group, tert-butyl group, n-pentyl group, sec-pentyl group, n-hexyl group, cyclohexyl group, n-heptyl group, n-octyl group, n-nonyl group, n-decyl group, fluoromethyl group, difluoromethyl group, trifluoromethyl group, chloromethyl group, dichloromethyl group, trichloromethyl group, bromomethyl group, dibromomethyl group, tribromomethyl group, fluoroethyl group, difluoroethyl group, trifluoroethyl group, chloroethyl group, dichloroethyl group, trichloroethyl group, bromoethyl group, dibromoethyl group, tribromoethyl group, hydroxymethyl group, hydroxyethyl group, hydroxylpropyl group, methoxy group, ethoxy group, n-propoxy group, n-butoxy group, n-pentyloxy group, sec-pentyloxy group, n-hexyloxy group, cyclohexyloxy group, n-heptyloxy group, n-octyloxy group, n-nonyloxy group, n-decyloxy group, trifluoromethoxy group, methylamino group, dimethylamino group, trimethylamino group, ethylamino group, and propylamino group.

Among the above described alkyl groups, methyl group, ethyl group, methoxy group, ethoxy group and trifluoromethyl group are preferred, from the viewpoint of steric hindrance and heat resistance.

From the viewpoint of improving the melt moldability of the polyimide compound, $L_1$ is more preferably a linking group selected from the following group of linking groups:

[Chem. 20]

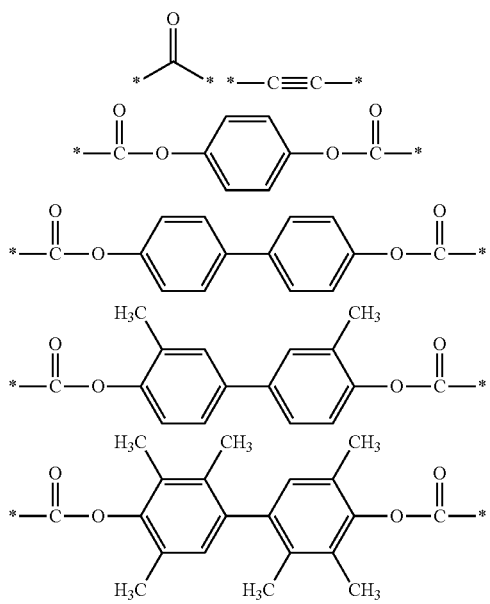

Accordingly, examples of the acid anhydride satisfying the general formula (2) or (3) include the following compounds:

[Chem. 21]

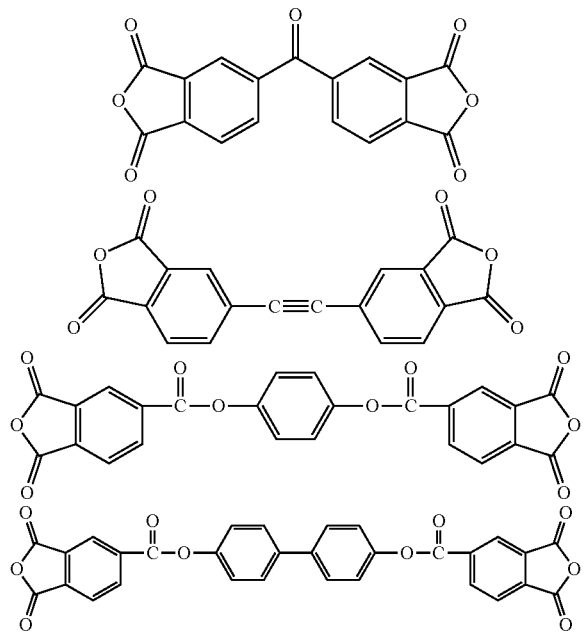

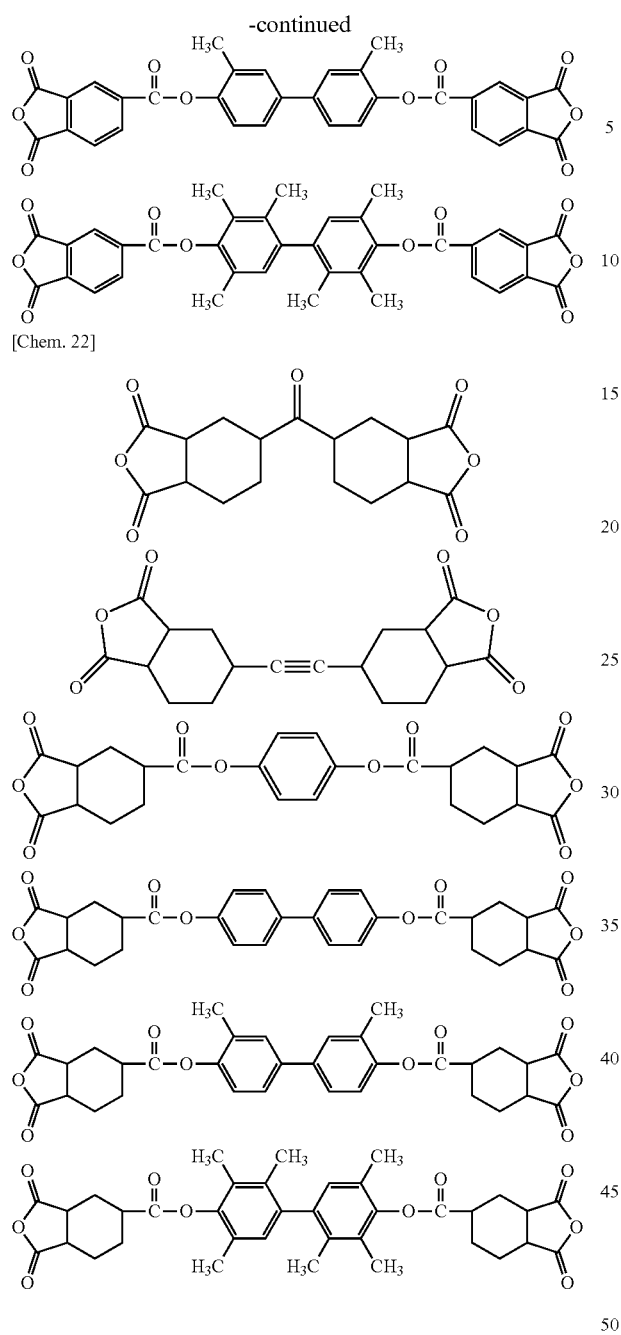

[Chem. 22]

[Chem. 23]

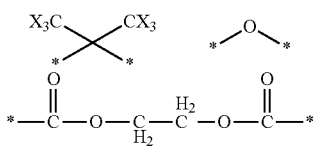

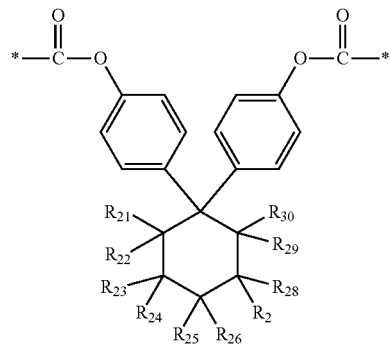

In the above described formulae,

X represents a halogen group selected from a fluoro group, a chloro group, a bromo group and an iodo group; and is preferably a fluoro group;

$R_{21}$ to $R_{30}$ are each independently selected from the group consisting of a hydrogen atom, a substituted alkyl group and an unsubstituted alkyl group; and

* represents a binding position.

The definition of the alkyl group is as described above.

From the viewpoint of improving the solubility in an organic solvent of the polyimide compound, $L_1$ is more preferably a linking group selected from the following group of linking groups:

[Chem. 24]

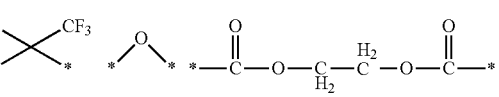

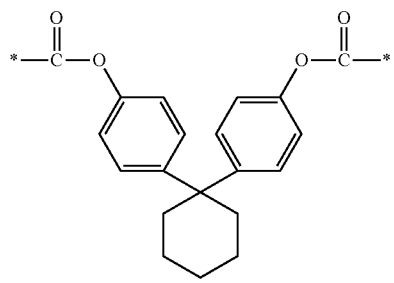

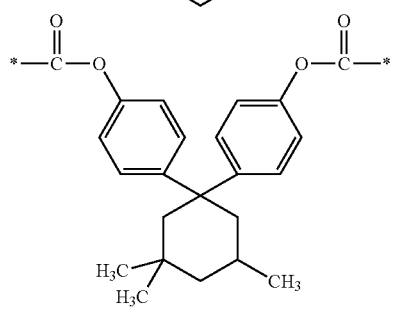

Accordingly, examples of the acid anhydride satisfying the general formula (2) or (3) include the following compounds:

[Chem. 25]

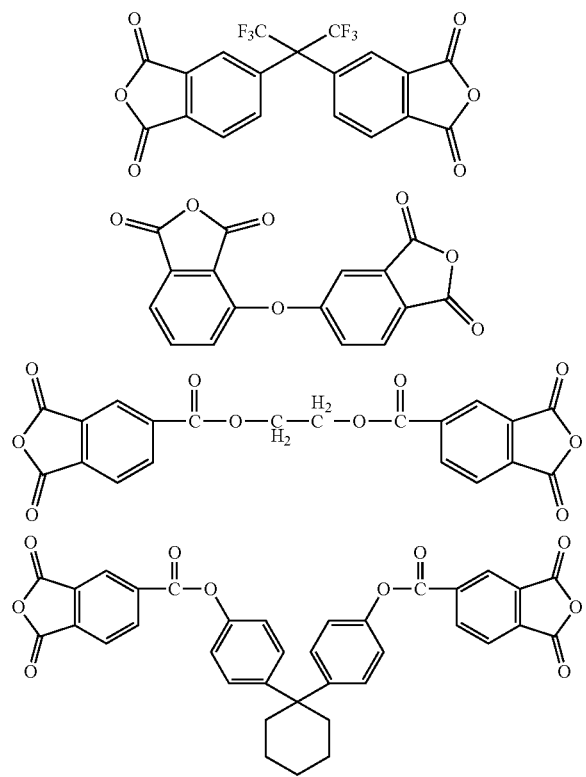

[Chem. 26]

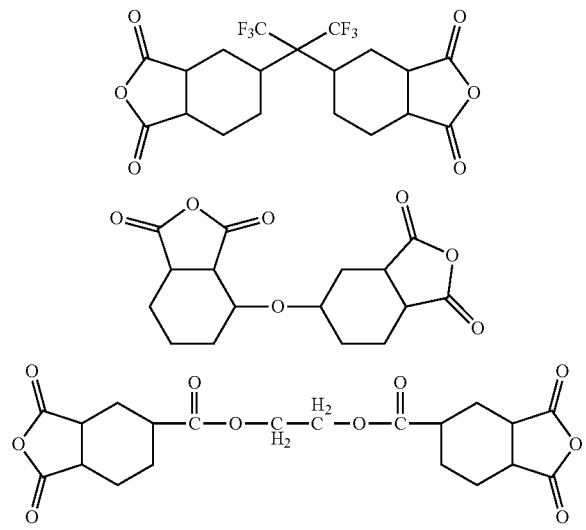

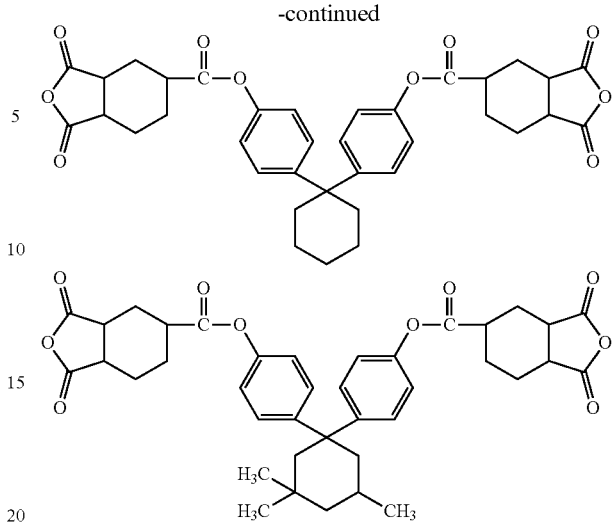

In the synthesis of the polyimide compound, two or more types of the acid anhydrides represented by the general formula(e) (8) and/or (9) may be used.

(Other Diamine Compounds)

The polyimide compound according to the present invention may contain another diamine compound, in addition to the diamine compound represented by the general formula (1).

Examples of the other diamine compound include m-phenylenediamine, p-phenylenediamine, 2,4-diaminotoluene, 2,4(6)-diamino-3,5-diethyltoluene, 5(6)-amino-1,3,3-trimethyl-1-(4-aminophenyl)-indan, 4,4'-diamino-2,2'-dimethyl-1,1'-biphenyl, 4,4'-diamino-2,2'-ditrifluoromethyl-1,1'-biphenyl, 4,4'-diamino-3,3'-dimethyl-1,1'-biphenyl, 3,4'-diaminodiphenyl ether, 4,4'-diaminodiphenyl ether, 3,3'-diaminodiphenyl sulfone, 4,4'-diaminodiphenyl sulfone, 4,4'-diaminodiphenyl sulfide, 4-aminophenyl-4-aminobenzoate, 4,4'-(9-fluorenylidene)dianiline, 9,9'-bis(3-methyl-4-aminophenyl)fluorene, 1,3-bis(3-aminophenoxy)benzene, 1,3-bis(4-aminophenoxy)benzene, 1,4-bis(4-aminophenoxy)benzene, 2,2-bis(4-aminophenyl)propane, 2,2-bis(3-methyl-4-aminophenyl)propane, 4,4'-(hexafluoroisopropylidene)dianiline, 2,2-bis(3-amino-4-methylphenyl)hexafluoropropane, 2,2-bis(3-methyl-4-aminophenyl)benzene, 2,2-bis[4-(4-aminophenoxy)phenyl]propane, 2,2-bis[4-(4-aminophenoxy)phenyl]hexafluoropropane, α,α-bis[4-(4-aminophenoxy)phenyl]-1,3-diisopropylbenzene, α,α-bis[4-(4-aminophenoxy)phenyl]-1,4-diisopropylbenzene, 3,7-diamino-dimethyldibenzothiophene-5,5-dioxide, bis(3-carboxy-4-aminophenyl)methylene, 3,3'-diamino-4,4'-dihydroxy-1,1'-biphenyl, 4,4'-diamino-3,3'-dihydroxy-1,1'-biphenyl, 2,2-bis(3-amino-4-hydroxyphenyl)propane, 2,2-bis(3-amino-4-hydroxyphenyl)hexafluoropropane, 1,3-bis(3-hydroxy-4-aminophenoxy)benzene, 2,2-bis(3-hydroxy-4-aminophenyl)benzene, and 3,3'-diamino-4,4'-dihydroxydiphenylsulfone.

The polyimide compound according to the present invention may contain one kind, or two or more kinds of the other diamine compounds described above, as a component(s).

The polyimide compound according to the present invention can be molded into a film or the like, as will be described later, and can be used as a base film or a cover film in a flexible printed wiring substrate (FPC). Further, the polyimide compound can also be used as an adhesive agent in a flexible wiring substrate or the like.

In addition to the above, the polyimide compound can also be used as an electrically insulating coating material for an electrical wire, a heat insulating material, a transparent substrate for a liquid crystal display element, a thin film transistor substrate or the like.

(Method of Synthesizing Polyimide Compound)

The polyimide compound according to the present invention can be produced by a conventionally known method, using a diamine compound represented by the above described general formula (1) and an acid anhydride. Specifically, the polyimide compound can be obtained by allowing the diamine compound to react with the acid anhydride to obtain a polyamide acid, and then carrying out a cyclodehydration reaction to convert the polyamide acid into a polyimide compound.

The mixing ratio of the acid anhydride and the diamine compound is preferably adjusted such that the total amount of the diamine compound is from 0.5% by mole to 1.5% by mole, and more preferably from 0.9% by mole to 1.1% by mole, with respect to 1% by mole of the total amount of the acid anhydride.

The reaction of the diamine compound with the acid anhydride is preferably carried out in an organic solvent.

The organic solvent is not particularly limited, as long as the solvent does not react with the diamine compound according to the present invention and with the acid anhydride, and capable of dissolving the reaction product of the diamine compound with the acid anhydride. Examples of such an organic solvent include N-methyl-2-pyrrolidone, N,N-dimethylformamide, N,N-dimethylacetamide, N,N'-dimethylimidazolidinone, γ-butyrolactone, dimethyl sulfoxide, sulfolane, 1,3-dioxolane, tetrahydrofuran, ethylene glycol monobutyl ether, ethylene glycol monoethyl ether, propylene glycol monomethyl ether, propylene glycol monoethyl ether, ethylene glycol dimethyl ether, ethylene glycol diethyl ether, ethylene glycol dibutyl ether, diethylene glycol dimethyl ether, diethylene glycol diethyl ether, diethylene glycol methyl ethyl ether, dipropylene glycol dimethyl ether, diethylene glycol dibutyl ether, dibenzyl ether, ethylene glycol monoethyl ether acetate, diethylene glycol monobutyl ether acetate, propylene glycol monomethyl ether acetate, propyl acetate, propylene glycol diacetate, butyl acetate, isobutyl acetate, 3-methoxybutyl acetate, 3-methyl-3-methoxybutyl acetate, benzyl acetate, butylcarbitol acetate, methyl lactate, ethyl lactate, butyl lactate, methyl benzoate, ethyl benzoate, triglyme, tetraglyme, acetylacetone, methyl propyl ketone, methyl butyl ketone, methyl isobutyl ketone, cyclopentanone, 2-heptanone, butyl alcohol, isobutyl alcohol, pentanol, 4-methyl-2-pentanol, 3-methyl-2-butanol, 3-methyl-3-methoxybutanol, diacetone alcohol, toluene and xylene.

From the viewpoint of improving the solubility of the polyimide compound according to the present invention, N-methyl-2-pyrrolidone, N,N'-dimethylimidazolidinone, γ-butyrolactone are preferred.

The diamine compound and the acid anhydride are preferably reacted at a reaction temperature of 40° C. or lower, in the case of carrying out the reaction by chemical imidization. In the case of carrying out the reaction by thermal imidization, in contrast, the reaction temperature is preferably from 150 to 220° C., and more preferably from 170 to 200° C.

When carrying out the cyclodehydration reaction, an imidization catalyst may be used. Examples of the imidization catalyst which can be used include: methylamine, ethylamine, trimethylamine, triethylamine, propylamine, tripropylamine, butylamine, tributylamine, tert-butylamine, hexylamine, triethanolamine, N,N-dimethylethanolamine, N,N-diethylethanolamine, triethylenediamine, N-methylpyrrolidine, N-ethylpyrrolidine, aniline, benzylamine, toluidine, trichloroaniline, pyridine, collidine, lutidine, picoline, quinolone, isoquinolone, and valerolactone.

Further, it is possible to use, as necessary, an azeotropic dehydrating agent, such as toluene, xylene or ethylcyclohexane, or an acid catalyst, such as acetic anhydride, propionic anhydride, butyric anhydride or benzoic acid anhydride.

In the reaction of the diamine compound with the acid anhydride, it is possible to use an end capping agent, such as benzoic acid, phthalic anhydride or hydrogenated phthalic anhydride.

Further, it is also possible to introduce a double bond or a triple bond at an end of the polyimide compound, by using, for example, maleic anhydride, ethynylphthalic anhydride, methylethynylphthalic anhydride, phenylethynylphthalic anhydride, phenylethynyltrimellitic anhydride, 3- or 4-ethynylaniline, or the like.

By introducing a double bond or a triple bond to the polyimide compound, the polyimide compound according to the present invention can be used as a thermosetting resin.

(Molded Product)

The molded product according to the present invention includes the polyimide compound obtained using the diamine compound represented by the general formula (1).

Examples of the molded article including the polyimide include: automotive parts such as cylinder head covers, bearing retainers, intake manifolds and pedals; casings and electronic material parts such as flexible printed circuit boards and printed wiring boards, used in personal computers and mobile phones; and fuel cell parts such as ion-conductive separators.

The shape of the molded product according to the present invention is not particularly limited, and it can be changed as appropriate, depending on the application thereof. For example, the molded product can be formed in the form of a film or a sheet.

In the molded product according to the present invention, the content of the polyimide compound obtained using the diamine compound represented by the general formula (1) is preferably 30% by mass or more and 100% by mass or less, more preferably 50% by mass or more and 100% by mass or less, and still more preferably 60% by mass or more and 100% by mass or less.

The molded product according to the present invention may include another compound to the extent that the properties of the molded product are not impaired. Examples of the other compound include polyolefin resins, polyester resins, cellulose resins, vinyl resins, polycarbonate resins, polyamide resins, styrene resins, and ionomer resins.

Further, the molded product according to the present invention may contain various types of additives, to the extent that the properties of the molded product are not impaired. Examples of the additives include: plasticizers, UV light stabilizers, stain inhibitors, matting agents, deodorants, flame retardants, weather resistant agents, antistatic agents, yarn friction reducing agents, slip agents, mold release agents, antioxidants, ion exchangers, dispersants and UV absorbers; and colorants such as pigments and dyes.

The molded product according to the present invention preferably has a 5% by weight reduction temperature of 350° C. or higher, and more preferably 400° C. or higher.

In the present invention, the 5% by weight reduction temperature of the molded product can be measured in accordance with JIS K 7120, using a thermomechanical analyzer (for example, TGA-50 (brand name); manufactured by Shimadzu Corporation) in nitrogen and at a temperature rise rate of 5° C./min.

The molded product according to the present invention preferably has a glass transition temperature (Tg) of 180° C. or higher, more preferably 190° C. or higher, and still more preferably 200° C. or higher.

In the present invention, the glass transition temperature (Tg) of the molded product can be measured in accordance with JIS K 7121, using a thermomechanical analyzer (brand name: DSC-60 Plus; manufactured by Shimadzu Corporation) under a stream of nitrogen gas and at a temperature rise rate of 10° C./min.

The molded product according to the present invention preferably has a melting temperature of 150° C. or higher, and more preferably 200° C. or higher. Further, the molded product has a melting temperature of 420° C. or lower, and more preferably 370° C. or lower.

In the present invention, the melting temperature of the molded product can be measured by a DSC measuring apparatus and/or a dynamic viscoelasticity measuring device.

The molded product according to the present invention preferably has a thermal expansion coefficient (CTE) of $70.0 \times 10^{-6}$/K or less, more preferably $65.0 \times 10^{-6}$/K or less, and still more preferably $60.0 \times 10^{-6}$/K or less.

In the present invention, the thermal expansion coefficient (CTE) of the molded product refers to the average thermal expansion coefficient (CTE) in the temperature range of from 100° C. to 250° C. Specifically, the average thermal expansion coefficient (CTE) is obtained by: heating the molded product from room temperature to 450° C. at a temperature rise rate of 10° C./min, using TMA-60 (brand name) manufactured by Shimadzu Corporation, while adding a load of 5 g thereto; and calculating the average value of the thermal expansion coefficients measured in the temperature range of from 100° C. to 250° C.

The molded product according to the present invention preferably has a tensile strength of 45 MPa or more, and more preferably 50 MPa or more, and still more preferably 60 MPa or more.

In the present invention, the tensile strength of the molded product refers to the average value of the tensile strengths in the MD direction and in the TD direction of the molded product, measured using a tensile tester (brand name: AG-X plus 50 kN; manufactured by Shimadzu Corporation) at a tensile speed of 10 mm/min.

The molded product according to the present invention preferably has an elastic modulus of 2.5 GPa or more, more preferably 3.0 GPa or more, and still more preferably 3.5 GPa.

The elastic modulus of the molded product according to the present invention refers to the average value of the elastic moduli in the MD direction and in the TD direction of the molded product, measured using a tensile tester (brand name: AG-X plus 50 kN; manufactured by Shimadzu Corporation) at a tensile speed of 10 mm/min.

The molded product according to the present invention preferably has a water absorption rate of 1.5% or less, and more preferably 1.0% or less.

The water absorption rate of the molded product according to the present invention can be obtained as follows. Specifically, the molded product is dipped in distilled water for 24 hours; water adhered to the surface of the molded product is wiped off with a waste cloth, followed by measuring the weight thereof; then the molded product is dried at 120° C. for 2 hours, followed by measuring the weight thereof; and calculating the rate of reduction in weight, to obtain the water absorption rate of the molded product.

(Method of Producing Molded Product)

In one embodiment, the molded product according to the present invention can be produced by dissolving the above described polyimide compound in the organic solvent, such as N-methyl-2-pyrrolidone (NMP), and coating the resulting solution on a substrate, such as a copper foil, followed by drying. In this manner, the molded product in the form of a film can be obtained.

Further, the substrate may be peeled off from the molded product, or the substrate may be removed by carrying out an etching treatment, depending on the application.

The molded product including the polyimide compound according to the present invention can be produced by a method consisting of the steps of: coating a polyisoimide compound or the polyimide compound on a substrate; and drying the coated compound. Accordingly, it is possible to omit a heat drying step which has been carried out in a conventional method, and which involves an imidization reaction and is performed at a high temperature. In addition, since the heat drying step can be omitted, it is possible to form the molded product according to the present invention on any of various types of substrates, without taking into consideration the heat resistance of the substrate.

Further, the molded product according to the present invention can be produced by a conventionally known method, such as press molding, transfer molding, injection molding or the like.

In another embodiment, the molded product according to the present invention can also be produced by a conventional method in which a polyamic acid solution or a polyisoimide solution is used.

For example, the diamine compound represented by the general formula (1) is allowed to react with the acid anhydride, suitably for a period of from 2 to 24 hours, while maintaining the temperature at 40° C. or lower, suitably within the range of from 0 to 25° C., and stirring the compounds in an organic solvent, to obtain a polyamic acid solution. The resulting polyamic acid solution is coated on a desired substrate (such as a copper foil), and the coated substrate is heat dried at a final drying temperature of from 250 to 450° C., more suitably from 350 to 400° C., to carry out imidization of the resulting polyamic acid compound. In this manner, a molded product including the polyimide compound according to the present invention can be formed on the substrate.

Further, the polyisoimide solution can be prepared by adding a dehydration condensation agent, such as N,N'-dicyclohexylcarbodiimide or trifluoroacetic anhydride, to the polyamic acid solution. By coating the thus prepared polyisoimide solution on a substrate, and heat drying the coated substrate, it is possible to form a molded product including the polyimide compound according to the present invention on the substrate.

In cases where N,N'-dicyclohexylcarbodiimide is used, it is preferred to remove N'-dicyclohexylurea generated in the reaction by filtration. Further, in cases where trifluoroacetic anhydride is used, it is preferred to use a poor solvent, such as methanol, in the isolation and purification of the polyisoimide compound. The isolated and purified polyisoimide compound can be thermally converted into a polyimide compound, by heating the polyisoimide compound at a temperature of 140° C. or higher, more preferably at a temperature of 180° C. or higher.

EXAMPLES

Example 1-1

Synthesis of Diamine Compound

To a 1 L four-necked flask equipped with a thermometer and a stirrer, 500 g of toluene, and 51.06 g (0.30 moles) of a commercially available product of o-phenylphenol (manufactured by Wako Pure Chemical Industries, Ltd.) were introduced. While cooling the resulting mixture and maintaining the reaction temperature within the range of from −5 to 0° C., 30 g (0.33 moles) of 70% by weight nitric acid (d=1.42) was added dropwise to the mixture over 2 hours. Further, the resultant was stirred at the same temperature for 3 hours, to complete the reaction.

The slurry of the resulting product was recovered by filtration, and washed with an aqueous solution of sodium hydrogen carbonate, and then with water.

Subsequently, the resultant was dried under reduced pressure, to obtain 2-hydroxy-5-aminobiphenyl represented by the following formula (5), having a color of pale yellow to yellow.

The purity of the resulting compound as measured by HPLC analysis (area %) was 97.01%, and the melting point as measured by DSC was 128° C. (endothermic peak). The analysis results were as follows: $^1$H-NMR (CDCl3) σ 5.84 ppm (1H of OH of phenol), σ 6.99 ppm (1H of o-position of phenol), σ 7.15 to 7.50 ppm (5H of o-phenyl), and σ 8.12 to 8.20 ppm (2H of m-position of phenol). The results confirmed that a nitro group was introduced at the p-position of phenol.

[Chem. 27]

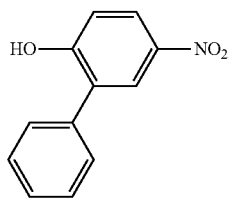

(5)

To a 1 L four-necked flask equipped with a thermometer, a stirrer and a reflux condenser, 43.04 g (0.20 moles) of 2-hydroxy-5-nitrobiphenyl synthesized as descried above, and 45.53 g (0.24 moles) of a commercially available product of 4-nitrobenzoyl chloride represented by the following formula (6), and 500 g of N,N'-dimethylformamide were introduced, and the resulting mixture was stirred while maintaining the temperature at approximately 15° C.

Subsequently, 30.36 g (0.30 moles) of triethylamine was slowly added to the mixture. After the completion of the addition, the reaction was allowed to proceed for 3 hours, while heating at 50° C. After the completion of the reaction, the reaction mixture was cooled to 25° C., and ion exchanged water was introduced thereinto, to obtain precipitates. After the temperature of the resultant reached 25° C., the precipitates were recovered by filtration, and washed with methanol and with ion exchanged water for a plurality of times, respectively. The washed precipitates were then dried under reduced pressure, to obtain a compound represented by the following formula (10).

[Chem. 28]

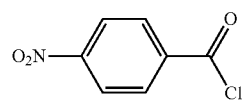

(6)

[Chem. 29]

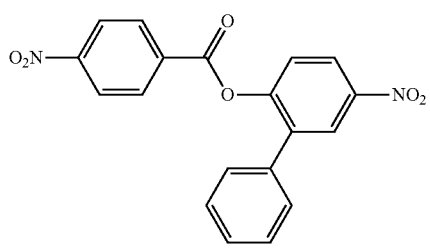

(10)

To a 500 cc autoclave equipped with a thermometer and a stirrer, 22 g (0.06 moles) of the compound represented by the chemical formula (10), 150 ml of dimethylacetamide, 5% Pd-carbon (as a dried product) were introduced, and the autoclave was replaced with nitrogen, and then replaced with hydrogen.

The compounds were then reduced, while maintaining the autoclave at a hydrogen pressure of 9 kg/cm2 (gauge pressure) and a temperature of 80° C., and the absorption of hydrogen stopped approximately after 2 hours. Further, the resultant was matured for 1 hour at 80° C., and then cooled to room temperature. After replacing the autoclave with nitrogen, the solution of the generated product was recovered, and the catalyst contained therein was removed by filtration. The filtrate was introduced into 50% methanol to allow precipitation of crystals, and the resulting crystals were collected.

The crystals were dried at 50° C. under vacuum, to obtain a diamine compound which satisfies the general formula (1) and which is represented by the following chemical formula (2). The purity of the resulting compound as measured by HPLC analysis (area %) was 99.04%, and the melting point as measured by DSC was 154° C. (endothermic peak).

Figure 2:
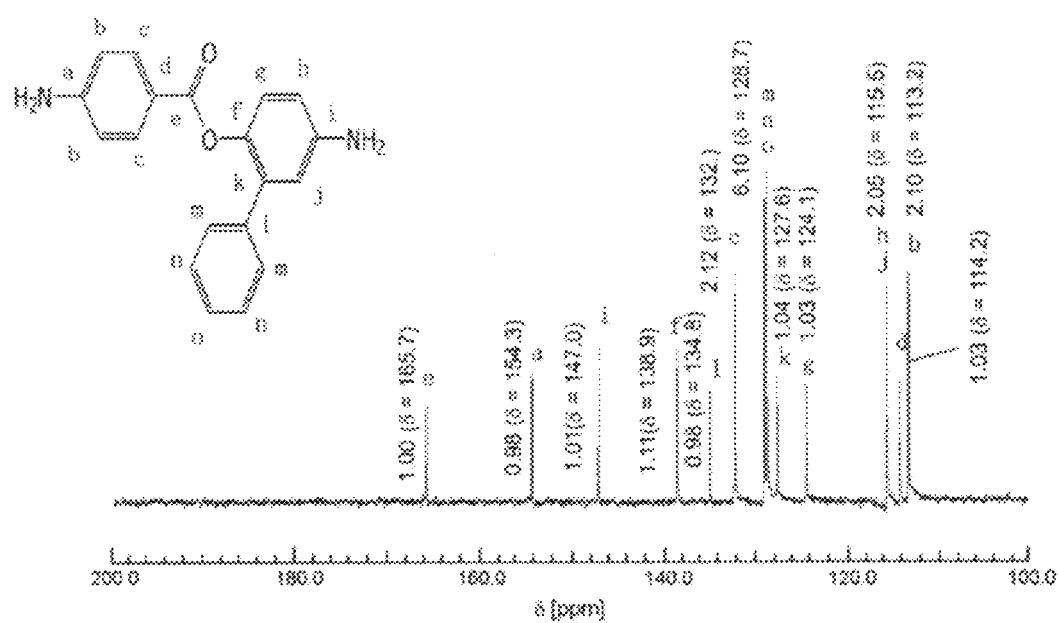
FIG. 2 is a ¹³C-NMR chart of the compound obtained in Examples and represented by the chemical formula (2).
Figure 3:
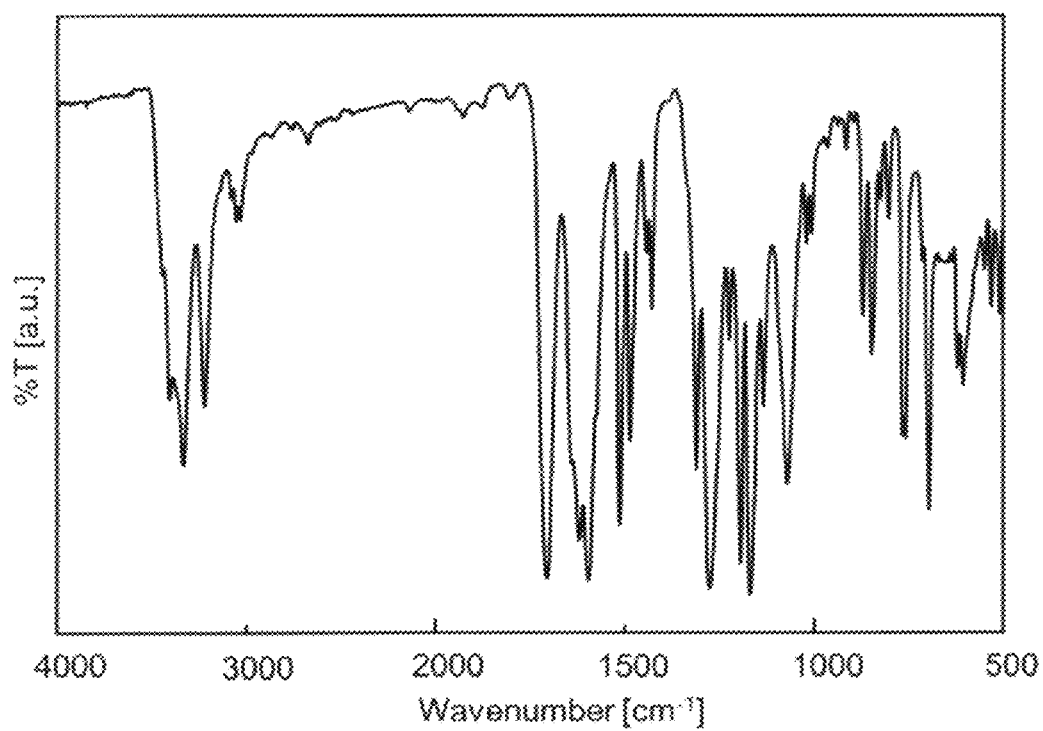
FIG. 3 is an FT-IR chart of the compound obtained in Examples and represented by the chemical formula (2).

Further, $^1$H-NMR, $^{13}$C-NMR, FT-IR and elemental analysis were carried out to identify the resulting compound and to confirm the structure thereof. As a result, it has been confirmed that the thus obtained compound was a compound represented by the chemical formula (2). The results of $^1$H-NMR (300 MHz; measuring apparatus: Varian 300-MR spectrometer; heavy solvent: DMSO-$d_6$), $^{13}$C-NMR (75 MHz; measuring apparatus: Varian 300-MR spectrometer; heavy solvent: DMSO-$d_6$) and FT-IR (KBr method; measuring apparatus: FTIR-410 spectrometer) are shown in FIGS. 1 to 3.

[Chem. 30]

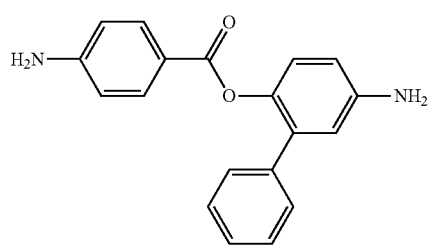

(2)

Synthesis of Polyimide Compound

To a 500 ml separable flask equipped with a nitrogen-introducing pipe and a stirring apparatus, 9.13 g (30 millimoles) of the diamine compound obtained as described above and represented by the chemical formula (2), 15.61 g (30 millimoles) of 4,4'-(4,4'-isopropylidenediphenoxy)bisphthalic dianhydride, 94.64 g of N-methyl-2-pyrrolidone, 0.47 g (6 millimoles) of pyridine, and 10 g of toluene were introduced. The resulting mixture was allowed to react for 4 hours at 180° C. under a nitrogen atmosphere, while removing toluene out of the system, during the reaction, to obtain 20% by weight of a polyimide solution. In the thus obtained polyimide solution, precipitation of the synthesized polyimide compound was not observed. In the DSC measurement, the glass transition temperature was observed at 207° C., and the synthesized polyimide compound was found to be an amorphous polyimide.

Example 1-2

Synthesis of Polyimide Compound

The same procedure as in Example 1-1 was repeated except that 10.75 g (30 millimoles) of 3,3',4,4'-biphenylsulfonetetracarboxylic dianhydride was used instead of 4,4'-(4,4'-isopropylidenediphenoxy)bisphthalic dianhydride, and N-methyl-2-pyrrolidone was used in an amount of 75.20 g, to obtain 20% by weight of a polyimide solution. In the thus obtained polyimide solution, precipitation of the synthesized polyimide compound was not observed. In the DSC measurement, an endothermic peak was observed at 271° C., and the synthesized polyimide compound was found to be a semicrystalline polyimide.

Comparative Example 1-1

Synthesis of Polyimide Compound

The same procedure as in Example 1-1 was repeated except that 6.85 g (30 millimoles) of 4-aminophenyl-4-aminobenzoate represented by the following formula was used instead of the diamine compound represented by the chemical formula (2), and N-methyl-2-pyrrolidone was used in an amount of 85.52 g, to prepare a polyimide solution. However, the synthesized polyimide compound had precipitated in the polyimide solution.

[Chem. 31]

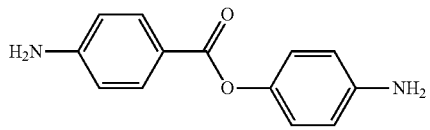

Comparative Example 1-2

Synthesis of Polyimide Compound

The same procedure as in Example 1-1 was repeated except that: 6.85 g (30 millimoles) of 4-aminophenyl-4-aminobenzoate was used instead of the diamine compound represented by the chemical formula (2); 10.75 g (30 millimoles) of 3,3',4,4'-biphenylsulfonetetracarboxylic dianhydride was used instead of 4'-(4,4'-isopropylidenediphenoxy)bisphthalic dianhydride; and N-methyl-2-pyrrolidone was used in an amount of 66.08 g; to prepare a polyimide solution. However, the synthesized polyimide compound had precipitated in the polyimide solution.

Example 2-1

Preparation of Molded Product

To a 500 mL separable flask equipped with a nitrogen-introducing pipe and a stirring apparatus, 8.83 g (30 millimoles) of 3,3',4,4'-biphenyltetracarboxylic dianhydride, 9.13 g (30 millimoles) of the diamine compound obtained as described above and represented by the chemical formula (2), and 67.52 g of N-methyl-2-pyrrolidone were introduced. The resulting mixture was stirred for 8 hours under a nitrogen atmosphere, to obtain 20% by weight of a polyamic acid solution.

The thus prepared polyamic acid solution was coated on a copper foil by a spin coating method, and dried at 100° C. for 0.5 hours, at 200° C. for 0.5 hours, at 300° C. for 2 hours, and then at 350° C. for 0.5 hours. Thereafter, the copper foil was removed by etching, to obtain a molded product in the form of a film having a thickness of about 15 µm.

Example 2-2

Preparation of Molded Product

The same procedure as in Example 2-1 was repeated except that 9.31 g (30 millimoles) of bis(3,4-dicarboxyphenyl) ether dianhydride was used instead of 3,3',4,4'-biphenyltetracarboxylic dianhydride, and N-methyl-2-pyrrolidone was used in an amount of 69.44 g, to obtain a molded product in the form of a film having a thickness of about 20 µm.

Reference Example 2-1

Preparation of Molded Product

The same procedure as in Example 2-1 was repeated except that: 6.85 g (30 millimoles) of 4-aminophenyl-4-aminobenzoate represented by the following formula was used instead of the diamine compound represented by the chemical formula (2); 8.83 g (30 millimoles) of 3,3',4,4'-biphenyltetracarboxylic dianhydride was used instead of pyromellitic dianhydride; and N-methyl-2-pyrrolidone was used in an amount of 58.40 g; to obtain a molded product in the form of a film having a thickness of about 20 µm.

[Chem. 32]

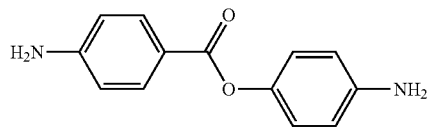

<<Performance Evaluation of Molded Product>>

<5% by weight Reduction Temperature>

The 5% by weight reduction temperature of each of the molded products obtained in the above described Examples and Comparative Examples was measured in accordance with JIS K 7120, using TGA-50 (brand name) manufactured by Shimadzu Corporation, in the air and at a temperature rise rate of 10° C./min. The measurement results are shown in Table 1.

<Glass Transition Temperature (Tg)>

The glass transition temperature (Tg) of each of the molded products obtained in the above described Examples and Comparative Examples was measured in accordance with JIS K 7121, using DSC-60 Plus (brand name) and TMA-60 (brand name) manufactured by Shimadzu Corporation, under a stream of nitrogen gas and at a temperature rise rate of 10° C./min. The measurement results are shown in Table 1.

<Melting Temperature>

The measurement of the melting temperature was also carried out using DSC-60 Plus (brand name) manufactured by Shimadzu Corporation and in the same manner as described above, and the apex of the endothermic peak was defined as the melting temperature (Tm). The measurement results are shown in Table 1.

<Thermal Expansion Coefficient (CTE)>

The molded products obtained in the above described Examples and Comparative Examples were each cut into a test piece having a size of 5 mm×20 mm. Using TMA-60 (brand name) manufactured by Shimadzu Corporation, each test piece was heated from room temperature to 450° C. at a temperature rise rate of 10° C./min, while applying a load of 5 g thereto, and the average thermal expansion coefficient (CTE) in the temperature range of from 100° C. to 250° C. was calculated for each test piece. The results are shown in Table 1.

<Tensile Strength>

The molded products obtained in the above described Examples and Comparative Examples were each cut into a test piece having a size of 10 mm×80 mm. Using a tensile tester (brand name: AG-X plus 50 kN; manufactured by Shimadzu Corporation), the tensile strength in the MD direction and the tensile strength in the TD direction of each test piece were measured, at a tensile speed of 10 mm/min. The average value of the tensile strength in the MD direction and the tensile strength in the TD direction was calculated for each test piece, and the results are shown in Table 1.

<Elastic Modulus>

The molded products obtained in the above described Examples and Comparative Examples were each cut into a test piece having a size of 10 mm× 80 mm. Using a tensile tester (brand name: AG-X plus 50 kN; manufactured by Shimadzu Corporation), the elastic modulus in the MD direction and the elastic modulus in the TD direction of each test piece were measured, at a tensile speed of 10 mm/min. The average value of the elastic modulus in the MD direction and the elastic modulus in the TD direction was calculated for each test piece, and the results are shown in Table 1.

<Water Absorption Rate>

The molded products obtained in the above described Examples and Comparative Examples were each cut into a test piece having a size of 50 mm×50 mm. Each test piece was dipped in distilled water for 24 hours, and after wiping off water adhered to the surface with a waste cloth, the weight of the test piece was measured. Subsequently, the test piece was dried at 120° C. for 2 hours, and the weight of the dried molded product was measured. The absorption rate of each test piece was determined from the rate of reduction in weight, and the results are shown in Table 1.

As is evident from Table 1, it has been found out that each of the molded products produced using the polyimide compound according to the present invention has a 5% by weight reduction temperature, a thermal expansion coefficient, a tensile strength, an elastic modulus and a water absorption rate, which are comparable to those of a molded product produced using a conventionally known polyimide compound, as well as a high heat resistance and high mechanical properties.

Further, it has become possible to produce a polyimide having a melting point, which is difficult to achieve by a conventional polyimide. This enabled the production of a highly heat resistant polyimide molded product which can be produced by melt molding, such as extrusion molding or injection molding.

TABLE 1

|  | 5% by weight reduction Temperature (° C.) | Glass transition temperature (° C.) | Melting temperature (° C.) | Thermal expansion coefficient ($10^{-6}$/K) | Tensile strength (MPa) | Elastic modulus (GPa) | Water absorption rate (%) |
| --- | --- | --- | --- | --- | --- | --- | --- |
| Example 2-1 | 517 | 262 | 360 | 10.3 | 182 | 8.5 | 0.4 |
| Example 2-2 | 506 | 229 | 411 | 23.6 | 105 | 5.4 | 0.3 |
| Reference Example 2-1 | 566 | — | — | 5.6 | 273 | 10.2 | 0.4 |

Example 3-1

Synthesis of Polyimide Compound

To a 500 ml separable flask equipped with a nitrogen-introducing pipe and a stirring apparatus, 30.43 g (100 millimoles) of the diamine compound obtained as described above, 44.43 g (100 millimoles) of an acid anhydride A represented by the following formula, 285 g of N-methyl-2-pyrrolidone, 1.6 g (20 millimoles) of pyridine, and 30 g of toluene were introduced. The resulting mixture was allowed to react for 6 hours at 180° C. under a nitrogen atmosphere, while removing toluene out of the system, during the reaction, to obtain 20% by weight of a polyimide solution. In the thus obtained polyimide solution, precipitation of the synthesized polyimide compound was not observed. In the DSC measurement, the glass transition temperature was observed at 258° C., and the synthesized polyimide compound was found to be an amorphous polyimide.

[Chem. 33]

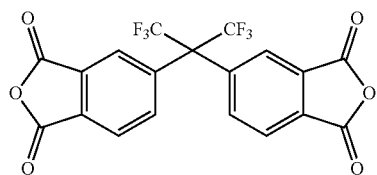

Example 3-2

Synthesis of Polyimide Compound

The same procedure as in Example 3-1 was repeated except that an acid anhydride B represented by the following formula was used instead of the acid anhydride A, to obtain a polyimide solution. In the thus obtained polyimide solution, precipitation of the synthesized polyimide compound was not observed. In the DSC measurement, the glass transition temperature was observed at 258° C., and the synthesized polyimide compound was found to be an amorphous polyimide.

[Chem. 34]

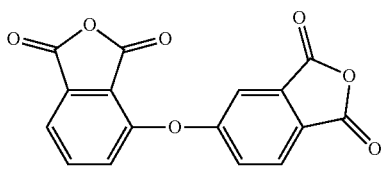

Example 3-3

Synthesis of Polyimide Compound

The same procedure as in Example 3-1 was repeated except that an acid anhydride C represented by the following formula was used instead of the acid anhydride A, to obtain a polyimide solution. In the thus obtained polyimide solution, precipitation of the synthesized polyimide compound was not observed. In the DSC measurement, the glass transition temperature was observed at 181° C., and the synthesized polyimide compound was found to be an amorphous polyimide.

[Chem. 35]

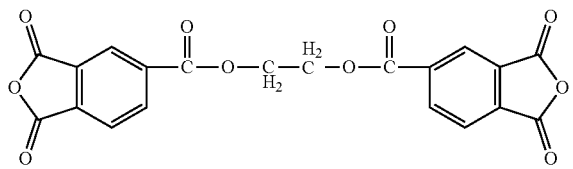

Example 3-4

Synthesis of Polyimide Compound

The same procedure as in Example 3-1 was repeated except that an acid anhydride D represented by the following formula was used instead of the acid anhydride A, to obtain a polyimide solution. In the thus obtained polyimide solution, precipitation of the synthesized polyimide compound was not observed. In the DSC measurement, the glass transition temperature was observed at 231° C., and the synthesized polyimide compound was found to be an amorphous polyimide.

[Chem. 36]

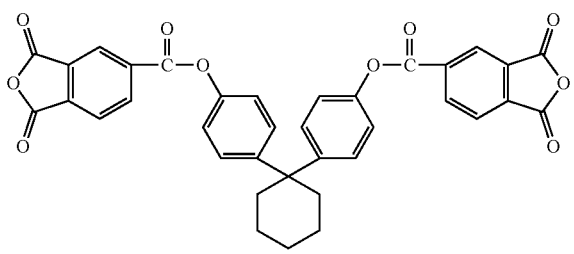

Example 3-5

Synthesis of Polyimide Compound

The same procedure as in Example 3-1 was repeated except that an acid anhydride E represented by the following formula was used instead of the acid anhydride A, to obtain a polyimide solution. In the thus obtained polyimide solution, precipitation of the synthesized polyimide compound was not observed. In the DSC measurement, the glass transition temperature was observed at 253° C., and the synthesized polyimide compound was found to be an amorphous polyimide.

[Chem. 37]

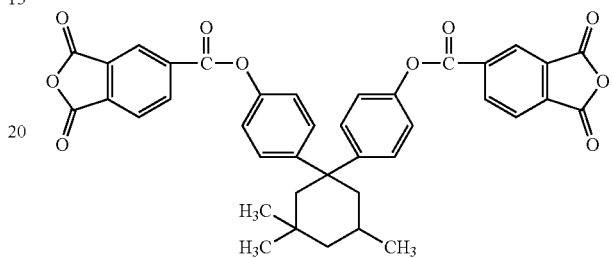

Example 4-1

Preparation of Molded Product

The polyimide acid solution prepared in Example 3-1 was coated on a copper foil by a spin coating method, and dried at 100° C. for 0.5 hours, at 200° C. for 0.5 hours, and then at 250° C. for 1 hour. Thereafter, the copper foil was removed by etching, to obtain a molded product in the form of a film having a thickness of about 15 μm.

Example 4-2

Preparation of Molded Product

The same procedure as in Example 3-1 was repeated except that the polyimide acid solution obtained in Example 3-2 was used as the polyimide acid solution, to obtain a molded product in the form of a film.

Example 4-3

Preparation of Molded Product

The same procedure as in Example 3-1 was repeated except that the polyimide acid solution obtained in Example 3-3 was used as the polyimide acid solution, to obtain a molded product in the form of a film.

Example 4-4

Preparation of Molded Product

The same procedure as in Example 3-1 was repeated except that the polyimide acid solution obtained in Example 3-4 was used as the polyimide acid solution, to obtain a molded product in the form of a film.

Example 4-5

Preparation of Molded Product

The same procedure as in Example 3-1 was repeated except that the polyimide acid solution obtained in Example 3-5 was used as the polyimide acid solution, to obtain a molded product in the form of a film.

<<Performance Evaluation of Molded Product>>

The 5% by weight reduction temperature, the glass transition temperature (Tg), the thermal expansion coefficient (CTE), the tensile strength and the elastic modulus of each of the molded products were measured in the same manner as described above, and the results are shown in Table 2.

TABLE 2

|  | 5% by weight reduction Temperature (° C.) | Glass transition temperature (° C.) | Thermal expansion coefficient ($10^{-6}$/K) | Tensile strength (MPa) | Elastic modulus (GPa) |
| --- | --- | --- | --- | --- | --- |
| Example 4-1 | 488 | 258 | 56 | 58 | 3.2 |
| Example 4-2 | 463 | 258 | 61 | 105 | 3.3 |
| Example 4-3 | 415 | 181 | 67 | 46 | 3.3 |
| Example 4-4 | 445 | 231 | 65 | 117 | 2.9 |
| Example 4-5 | 437 | 253 | 66 | 99 | 3.1 |

Example 5-1

Preparation of Molded Product

To a 500 mL separable flask equipped with a nitrogen-introducing pipe and a stirring apparatus, 32.22 g (100 millimoles) of an acid anhydride F represented by the following formula, 30.43 g (100 millimoles) of the diamine compound obtained in the above described Reference Example, and 236 g of N-methyl-2-pyrrolidone were introduced. The resulting mixture was allowed to react for 8 hours under a nitrogen atmosphere, to obtain 20% by weight of a polyamide acid solution.

The thus obtained polyamide acid solution was coated on a copper foil by a spin coating method, and dried at 100° C. for 0.5 hours, at 200° C. for 0.5 hours, at 300° C. for 1 hour, and then at 350° C. for 0.5 hours. Thereafter, the copper foil was removed by etching, to obtain a molded product in the form of a film having a thickness of about 15 μm.

[Chem. 38]

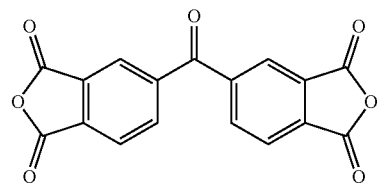

Example 5-2

Preparation of Molded Product Including Polyimide Compound

The same procedure as in Example 5-1 was repeated except that an acid anhydride G represented by the following formula was used instead of the acid anhydride F, to obtain a molded product in the form of a film.

[Chem. 39]

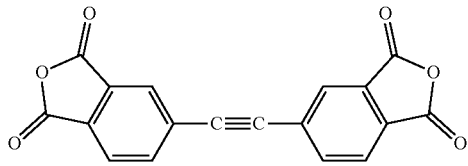

Example 5-3

Preparation of Molded Product Including Polyimide Compound

The same procedure as in Example 5-1 was repeated except that an acid anhydride H represented by the following formula was used instead of the acid anhydride F, to obtain a molded product in the form of a film.

[Chem. 40]

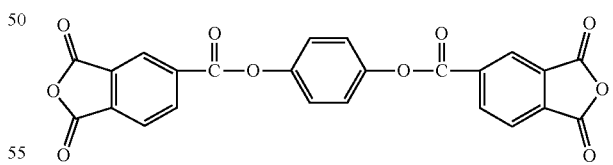

Example 5-4

Preparation of Molded Product Including Polyimide Compound

The same procedure as in Example 5-1 was repeated except that an acid anhydride I represented by the following formula was used instead of the acid anhydride F, to obtain a molded product in the form of a film.

[Chem. 41]

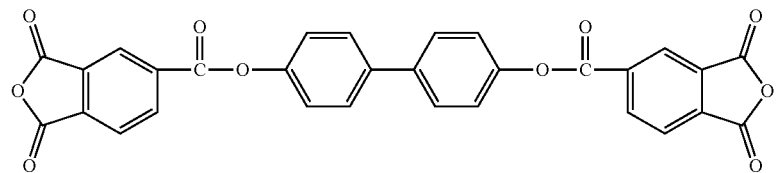

Example 5-5

Preparation of Molded Product Including Polyimide Compound

The same procedure as in Example 5-1 was repeated except that an acid anhydride J represented by the following formula was used instead of the acid anhydride F, to obtain a molded product in the form of a film.

[Chem. 42]

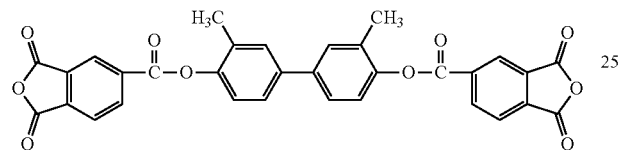

Example 5-6

Preparation of Molded Product Including Polyimide Compound

The same procedure as in Example 5-1 was repeated except that an acid anhydride K represented by the following formula was used instead of the acid anhydride F, to obtain a molded product in the form of a film.

[Chem. 43]

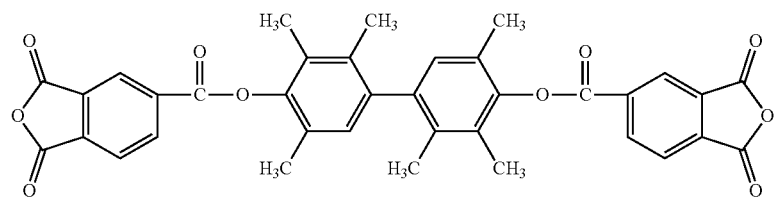

<<Performance Evaluation of Molded Product>>

The 5% by weight reduction temperature, the glass transition temperature (Tg), the melting temperature, the thermal expansion coefficient (CTE), the tensile strength and the elastic modulus of each of the molded products were measured in the same manner as described above, and the results are shown in Table 3.

TABLE 3

| | 5% by weight reduction Temperature (° C.) | Glass transition temperature (° C.) | Melting temperature (° C.) | Thermal expansion coefficient ($10^{-6}$/K) | Tensile strength (MPa) | Elastic modulus (GPa) |
|---|---|---|---|---|---|---|
| Example 5-1 | 487 | 289 | 367 | 37 | 126 | 5.6 |
| Example 5-2 | 355 | — | 356 | 10 | 130 | 4.0 |

TABLE 3-continued

|  | 5% by weight reduction Temperature (° C.) | Glass transition temperature (° C.) | Melting temperature (° C.) | Thermal expansion coefficient ($10^{-6}$/K) | Tensile strength (MPa) | Elastic modulus (GPa) |
|---|---|---|---|---|---|---|
| Example 5-3 | 466 | 215 | 354 | 20 | 106 | 7.2 |
| Example 5-4 | 477 | 193 | 355 | 24 | 111 | 5.7 |
| Example 5-5 | 460 | 230 | 331 | 27 | 52 | 5.6 |
| Example 5-6 | 457 | 236 | 355 | 51 | 68 | 6.4 |

The invention claimed is:

1. A polyamide acid which is a reaction product of the diamine compound represented by the following general formula (1) with an acid anhydride :

[Chem. 1]

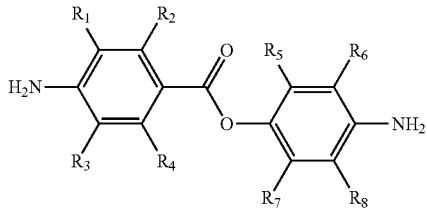

(1)

(wherein
  $R_1$ to $R_8$ are each independently selected from the group consisting of a hydrogen atom, a fluorine atom, a substituted or unsubstituted alkyl group, and a substituted or unsubstituted aromatic group; and
  at least one of $R_1$ to $R_8$ is a substituted or unsubstituted aromatic group).

2. The polyamide acid according to claim 1, wherein one or two of $R_5$ to $R_8$ is/are (each) a substituted or unsubstituted aromatic group.

3. The polyamide acid according to claim 1, wherein one or two of $R_5$ to $R_8$ is/are (each) a substituted or unsubstituted aromatic group, and $R_1$ to $R_8$ other than the aromatic group(s) are each selected from the group consisting of a hydrogen atom, a fluorine atom, and a substituted or unsubstituted alkyl group.

4. The polyamide acid according to claim 1, wherein the substituted or unsubstituted aromatic group has from 5 to 20 carbon atoms.

5. The polyamide acid according to claim 1, wherein the substituted or unsubstituted aromatic group is selected from the group consisting of a phenyl group, a methylphenyl group, a phenoxy group, a benzyl group and a benzyloxy group.

6. The polyamide acid according to claim 1, wherein the acid anhydride is represented by the following general formula(e) (8) and/or (9):

[Chem. 2]

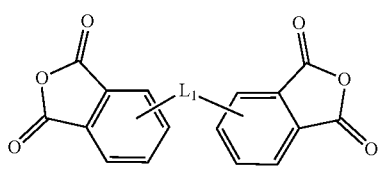

(8)

[Chem. 3]

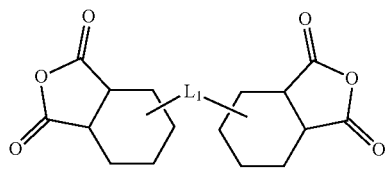

(9)

(wherein
  $L_1$ represents a linking group selected from the following group of linking groups:

[Chem. 4]

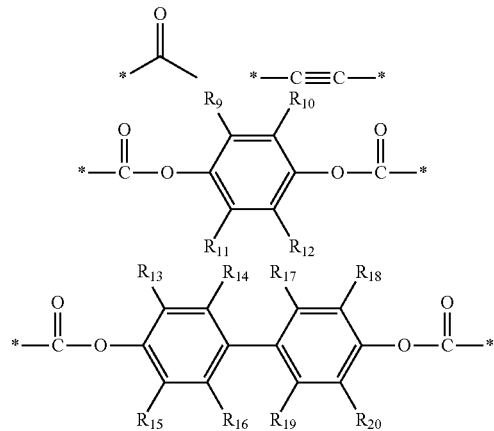

wherein
  $R_9$ to $R_{20}$ are each independently selected from the group consisting of a hydrogen atom, a substituted alkyl group and an unsubstituted alkyl group; and * represents a binding position).

7. The polyamide acid according to claim 1, wherein the acid anhydride is represented by the following general formula(e) (8) and/or (9):

[Chem. 5]

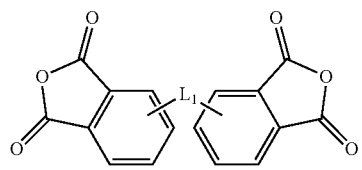

(8)

[Chem. 6]

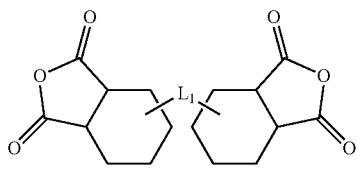
(9)

(wherein

L₁ represents a linking group selected from the following group of linking groups:

[Chem. 7]

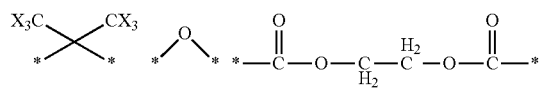

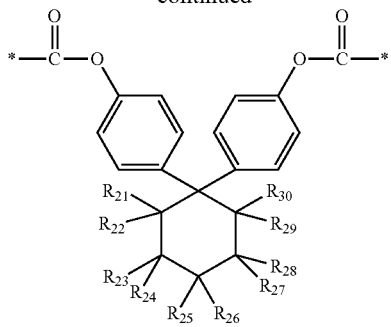

wherein

X represents a halogen group selected from a fluoro group, a chloro group, a bromo group and an iodo group;

$R_{21}$ to $R_{30}$ are each independently selected from the group consisting of a hydrogen atom, a substituted alkyl group and an unsubstituted alkyl group; and

* represents a binding position).

* * * * *